United States Patent
Park et al.

(10) Patent No.: US 12,274,419 B2
(45) Date of Patent: Apr. 15, 2025

(54) MICRO-ROBOT CONTROL APPARATUS

(71) Applicant: KOREA INSTITUTE OF MEDICAL MICROROBOTICS, Gwangju (KR)

(72) Inventors: Jongoh Park, Gyeonggi-do (KR); Chang-Sei Kim, Gwangju (KR); Eunpyo Choi, Gwangju (KR); Jayoung Kim, Daejeon (KR); Byungjeon Kang, Gwangju (KR); Manh Cuong Hoang, Gwangju (KR); Ayoung Hong, Daegu (KR)

(73) Assignee: KOREA INSTITUTE OF MEDICAL MICROROBOTICS, Gwangju (KR)

( * ) Notice: Subject to any disclaimer, the term of this patent is extended or adjusted under 35 U.S.C. 154(b) by 988 days.

(21) Appl. No.: 17/298,983

(22) PCT Filed: Feb. 10, 2020

(86) PCT No.: PCT/KR2020/001806
§ 371 (c)(1),
(2) Date: Jun. 2, 2021

(87) PCT Pub. No.: WO2020/171446
PCT Pub. Date: Aug. 27, 2020

(65) Prior Publication Data
US 2022/0061642 A1 Mar. 3, 2022

(30) Foreign Application Priority Data

Feb. 19, 2019 (KR) .................. 10-2019-0019443
Dec. 13, 2019 (KR) .................. 10-2019-0166881

(51) Int. Cl.
*A61B 34/00* (2016.01)
*A61B 1/00* (2006.01)
(Continued)

(52) U.S. Cl.
CPC .......... *A61B 1/041* (2013.01); *A61B 1/00036* (2013.01); *A61B 1/00158* (2013.01);
(Continued)

(58) Field of Classification Search
CPC .................................................. A61N 2/00–12
See application file for complete search history.

(56) References Cited

U.S. PATENT DOCUMENTS 3,337,776 A * 8/1967 Elmi .................. A61N 2/02
600/13
4,495,953 A * 1/1985 Bennewitz .............. A61F 11/04
607/136
(Continued)

FOREIGN PATENT DOCUMENTS

JP 2002-355264 A 12/2002
JP 2005-052637 A 3/2005
(Continued)

OTHER PUBLICATIONS

International Search Report from corresponding PCT Application No. PCT/KR2020/001806, dated Jun. 9, 2020.

*Primary Examiner* — Thaddeus B Cox
(74) *Attorney, Agent, or Firm* — Harness, Dickey & Pierce, P.L.C.

(57) ABSTRACT

The present invention relates to a micro-robot control apparatus. An electromagnetic module for focusing magnetic field and a micro-robot control apparatus comprising the electromagnetic module, according to the present invention, focus the magnetic field in an area of interest where focusing of same is desired to allow a micro-robot to be controlled, and, the apparatus having been simplified, allow efficient setup and operation in the surgery area. Moreover, the number of electromagnets is reduced to thus reduce the number of sources of power, thereby resulting in efficient operation of the apparatus with lowered power consumption.

(Continued)

Additionally, by means of a magnetic induction frequency signal reception coil of the micro-robot and the external micro-robot control apparatus equipped with a magnetic induction transmission coil, the micro-robot control apparatus can both generate power wirelessly for the micro-robot, and implementation location recognition of same due to the efficiency of the generated power.

23 Claims, 26 Drawing Sheets

(51) Int. Cl.
  *A61B 1/04*   (2006.01)
  *A61B 1/045*  (2006.01)
  *A61N 2/02*   (2006.01)
(52) U.S. Cl.
  CPC .............. *A61B 1/045* (2013.01); *A61B 34/72* (2016.02); *A61N 2/02* (2013.01)

(56) References Cited

U.S. PATENT DOCUMENTS

| | | | | |
|---|---|---|---|---|
| 5,353,807 | A | * 10/1994 | DeMarco | A61M 25/0127 600/585 |
| 2014/0081169 | A1 | * 3/2014 | Gerding | A61K 31/194 600/560 |
| 2015/0018614 | A1 | * 1/2015 | Duan | A61B 1/041 600/109 |
| 2019/0025040 | A1 | * 1/2019 | Andreason | A61B 5/062 |

FOREIGN PATENT DOCUMENTS

| | | |
|---|---|---|
| JP | 2008-029864 A | 2/2008 |
| KR | 10-0972253 B1 | 7/2010 |
| KR | 10-2016-0101441 A | 8/2016 |
| KR | 10-1647020 B1 | 8/2016 |
| KR | 10-2017-0099232 A | 8/2017 |

\* cited by examiner

MICRO-ROBOT CONTROL APPARATUS

CROSS-REFERENCE TO RELATED APPLICATIONS

This application is a national phase application of PCT Application No. PCT/KR2020/001806 filed on Feb. 10, 2020, which claims the benefit of and priority to Korean Patent Application Nos. 10-2019-0019443 filed on Feb. 19, 2019 and 10-2019-0166881 filed on Dec. 13, 2019. The entire disclosures of the applications identified in this paragraph are incorporated herein by references.

TECHNICAL FIELD

The present disclosure has been made according to project number HI19C0642 under the support of the Ministry of Health and Welfare, the research management institution for the above project is the Korea Health Industry Development Institute, the title of the research business is "Development of Technology and Commercialization for Medical Micro-robots", the title of the research project is "Common Basis Technology Development Center for Commercialization of Medical Micro-robots", the host organization thereof is the Korea Institute of Medical Micro-robotics, and the research period thereof is Jun. 12, 2019 to Dec. 31, 2022.

This patent application claims priority from Korean Patent Application No. 10-2019-0166881, filed with the Korean Intellectual Property Office on Dec. 13, 2019, which is hereby incorporated by reference.

The present disclosure relates to a micro-robot control apparatus.

BACKGROUND ART

Electromagnetic field devices are being developed to drive micro-robots, which are located inside the human body, from the outside of the human body. Wired or wireless micro-robots are utilized according to the purpose of intra-body procedures, and technologies for driving micro-robots by controlling the direction and intensity of a magnetic field through an electromagnetic field devices have been known or are being developed. Specifically, for example, an electromagnetic field device having a plurality of electromagnets/permanent magnets disposed in consideration of the disease site in the human body and the motion characteristics of a micro-robot, and having a fixed or mobile system structure are under development.

Existing electromagnetic field driving devices have a large number of electromagnets in use and thus are large in size, thereby failing to provide efficient installation and operation of the devices. Further, the large number of electromagnets causes an increase in the number of power supplies, thereby resulting in an increase in power consumption, which is inefficient in terms of various operations.

In addition, a magnetic field driving device using permanent magnets has a small number of magnets in use, but has a limitation in controlling a micro-robot. Further, the robot is driven through a change of the distance between the robot and the magnet and a change of the direction of the magnet, and since the permanent magnet has a constant magnetization value, there is limited control performance. Although a control space of the permanent magnet is secured using a motor, it is difficult to control the magnetic field in real time due to the time difference in the movement by the motor.

In the case of a conventional method of controlling a robot by changing a gradient magnetic field and a uniform magnetic field in space, it is difficult to focus the robot to a desired location without location information.

In addition, since the micro-robot (a capsule endoscope or the like) inserted into the human body is configured in micro units depending on the purpose, if the micro-robot is inserted into the human body, it is difficult to recognize the exact location of the capsule endoscope while it moves.

In particular, in order to recognize the location of the capsule endoscope inside the human body, a technology for recognizing the location of the capsule endoscope using RF (radio frequency) signals is being developed, but this technology has a problem with location errors because the transmission characteristics of RF signals through the human body differ. Although a location recognition technology is being developed through an array of Hall sensors for measuring magnetic field components, efficiency of measuring the magnetic field is lowered depending on the distance between the Hall sensor and the capsule, thereby causing location errors.

Meanwhile, a technology capable of identifying the location of a capsule from an image photographed by a dual-source X-ray imaging apparatus using two X-ray sources has been disclosed. The dual-source X-ray imaging apparatus, which includes two X-ray sources disposed perpendicular to each other so as to radiate X-rays onto the top and side surfaces of an object to be photographed and two X-ray detectors located to face the two X-ray sources, respectively, may obtain 2D images on the top and side surfaces of the object to be photographed, and may obtain 3D image information by matching the same, thereby recognizing the location of the capsule endoscope inside the human body. However, location recognition using the X-ray information requires a large configuration of a system, which increases the cost.

In order to solve the problems of the prior art described above, the present inventors have made the present disclosure including an electromagnetic module for controlling a micro-robot, a system for recognizing the location of a micro-robot, and a micro-robot control apparatus using the same.

SUMMARY

Technical Problem

The present disclosure has been made to solve the above-described problems in the prior art, and an objective of the present disclosure is to provide an electromagnetic module for focusing a magnetic field which is capable of focusing a magnetic field on a desired area of interest using only a pair of (two) electromagnetic modules and controlling a micro-robot inside the human body according thereto.

Another objective of the present disclosure is to provide a micro-robot control apparatus including the dual electromagnetic module described above.

Another objective of the present disclosure is to provide a micro-robot control apparatus including a dual electromagnetic module for focusing a magnetic field which is capable of focusing a magnetic field on a desired area of interest using only a pair of (two) electromagnetic modules and controlling a micro-robot inside the human body according thereto, and a magnetic induction transmission coil configured to generate a magnetic induction frequency signal for recognizing the location of the micro-robot.

Another objective of the present disclosure is to provide a micro-robot control apparatus including a dual electromagnetic module for focusing a magnetic field configured to focus a magnetic field on a desired area of interest using only a pair of (two) electromagnetic modules and control a micro-robot inside the human body through the same, a magnetic induction transmission coil configured to generate a magnetic induction frequency signal for recognizing the location of the micro-robot, a moving part configured to control a rotational motion of the two electromagnetic modules with respect to a symmetric axis and a three-dimensional linear motion thereof, and a micro-robot equipped with a magnetic induction frequency signal reception coil for location recognition, wherein a core protrusion is formed at one of either end of the two electromagnetic modules, which is close to the area of interest.

Technical Solution

In order to attain the objectives described above, an electromagnetic module for focusing a magnetic field according to an aspect of the present disclosure includes two electromagnetic modules including a magnetic core made of a paramagnet and a solenoid coil wound around the magnetic core, wherein the two electromagnetic modules are disposed to be symmetrical with each other with respect to an imaginary symmetric axis passing through the center of an area of interest, where a magnetic field is desired to be focused, on a two-dimensional plane including the symmetric axis.

In an embodiment of the present disclosure, a core protrusion may be formed at one of either end of the two electromagnetic modules, which is close to the area of interest.

In an embodiment of the present disclosure, the electromagnetic module for focusing a magnetic field may further include a rotatable spherical paramagnet disposed in a space between the core protrusions of the two electromagnetic modules and the area of interest.

In an embodiment of the present disclosure, the core protrusions of the two electromagnetic modules may be disposed adjacent to each other.

In an embodiment of the present disclosure, the core protrusion may have a cylindrical shape having the same diameter as the inner diameter of the solenoid coil.

In an embodiment of the present disclosure, the diameter of a portion at which a protrusion starts in the core protrusion may be the same as the inner diameter of the solenoid coil, and the diameter of the end of the core protrusion may be smaller than the inner diameter of the solenoid coil. More specifically, for example, the core protrusion may have a shape of a truncated cone or a combination of a cylinder and a truncated cone.

In an embodiment of the present disclosure, the core protrusion may have a cylindrical shape having the same diameter as the outer diameter of the solenoid coil.

In order to attain the objectives described above, a micro-robot control apparatus according to another aspect of the present disclosure may include: the electromagnetic module; a power source configured to supply power to the solenoid coil of the electromagnetic module; and a moving part configured to control a rotational motion of the electromagnetic module with respect to the symmetric axis and a three-dimensional linear motion thereof.

In order to attain the objectives described above, a micro-robot control apparatus according to another aspect of the present disclosure may include two electromagnetic modules including magnetic cores made of paramagnets that are disposed to be symmetrical with each other with respect to an imaginary symmetric axis passing through the center of an area of interest, where the magnetic field is desired to be focused, on a two-dimensional plane including the symmetric axis, and solenoid coils wound around the magnetic cores; a magnetic induction transmission coil configured to generate a magnetic induction frequency signal for recognizing the location of a micro-robot; and a power source configured to supply power to the solenoid coils of the electromagnetic module and the magnetic induction transmission coil. At this time, the two electromagnetic modules may include all embodiments of the above-described two electromagnetic modules.

In an embodiment of the present disclosure, the micro-robot control apparatus may further include a moving part configured to control a rotational motion of the two electromagnetic modules with respect to the symmetric axis and a three-dimensional linear motion thereof.

In an embodiment of the present disclosure, the micro-robot control apparatus may further include a micro-robot equipped with a magnetic induction frequency signal reception coil for recognition of location.

In an embodiment of the present disclosure, the magnetic induction transmission coil may apply a magnetic induction frequency signal to the micro-robot, and the micro-robot control apparatus may receive the amount of electromotive force induced by the micro-robot, and may then recognize the location of the micro-robot in 6 degrees of freedom.

In an embodiment of the present disclosure, the amount of electromotive force induced by the micro-robot may be converted based on distance to recognize the location of the micro-robot in 6 degrees of freedom.

In an embodiment of the present disclosure, the location of the micro-robot in 6 degrees of freedom recognized by the micro-robot control apparatus may include three-dimensional coordinate information and rotational angle information at respective coordinates.

In an embodiment of the present disclosure, the micro-robot may be a capsule endoscope including: a body in the form of a capsule; a magnetic induction frequency signal reception coil configured to generate induction power from the magnetic induction frequency signal applied for recognition of location; a charging module configured to be charged by the induced power; a magnet configured to interact with an external magnetic field; and an RF (radio frequency) coil configured to transmit a frequency signal of the induced power generated from the magnetic induction frequency signal reception coil to the micro-robot control apparatus.

In an embodiment of the present disclosure, in order to attain the objectives described above, a micro-robot control apparatus according to another aspect of the present disclosure may include: two electromagnetic modules including magnetic cores made of paramagnets that are disposed to be symmetrical with each other with respect to an imaginary symmetric axis passing through the center of an area of interest, where the magnetic field is desired to be focused, on a two-dimensional plane including the symmetric axis, and solenoid coils wound around the magnetic cores; a magnetic induction transmission coil configured to generate a magnetic induction frequency signal for recognizing the location of a micro-robot; a power source configured to supply power to the solenoid coils of the electromagnetic module and the magnetic induction transmission coil; a moving part configured to control a rotational motion of the two electromagnetic modules with respect to the symmetric axis and a three-dimensional linear motion thereof; and a micro-robot equipped with a magnetic induction frequency signal reception coil for recognition of location, wherein a core protrusion may be formed at one of either end of the two electromagnetic modules, which is close to the area of interest. At this time, the configurations related to the two electromagnetic modules and recognition of the location of the micro-robot may include all of the embodiments described in detail.

Advantageous Effects

The electromagnetic module for focusing a magnetic field according to the present disclosure and a micro-robot control apparatus including the same use a dual electromagnetic module in a simple structure including two electromagnetic modules including a magnetic core configured as a paramagnet and a solenoid coil wound around the magnetic core, thereby controlling the micro-robot by focusing a magnetic field on the area of interest where the magnetic field is desired to be focused and simplifying the device, which makes it possible to provide efficient installation and operation of the device in the surgery area. In addition, it is possible to reduce the number of power supplies by reducing the number of electromagnets, and to secure efficient operation of the device by reducing power consumption thereof.

In addition, the micro-robot control apparatus according to the present disclosure makes it possible to simultaneously perform generation of wireless power of the micro-robot and location recognition thereof according to the efficiency of the generated power using a micro-robot control apparatus equipped with an external magnetic induction transmission coil and a magnetic induction frequency signal reception coil of the micro-robot. In addition, the micro-robot control apparatus enables recognition of the location of the micro-robot in 6 degrees of freedom using locations in three directions and angles in three directions, so it is possible to solve the locational errors caused by the characteristics of the human body and the characteristics of the sensor device.

BEST MODE FOR CARRYING OUT THE INVENTION

Figure 1:
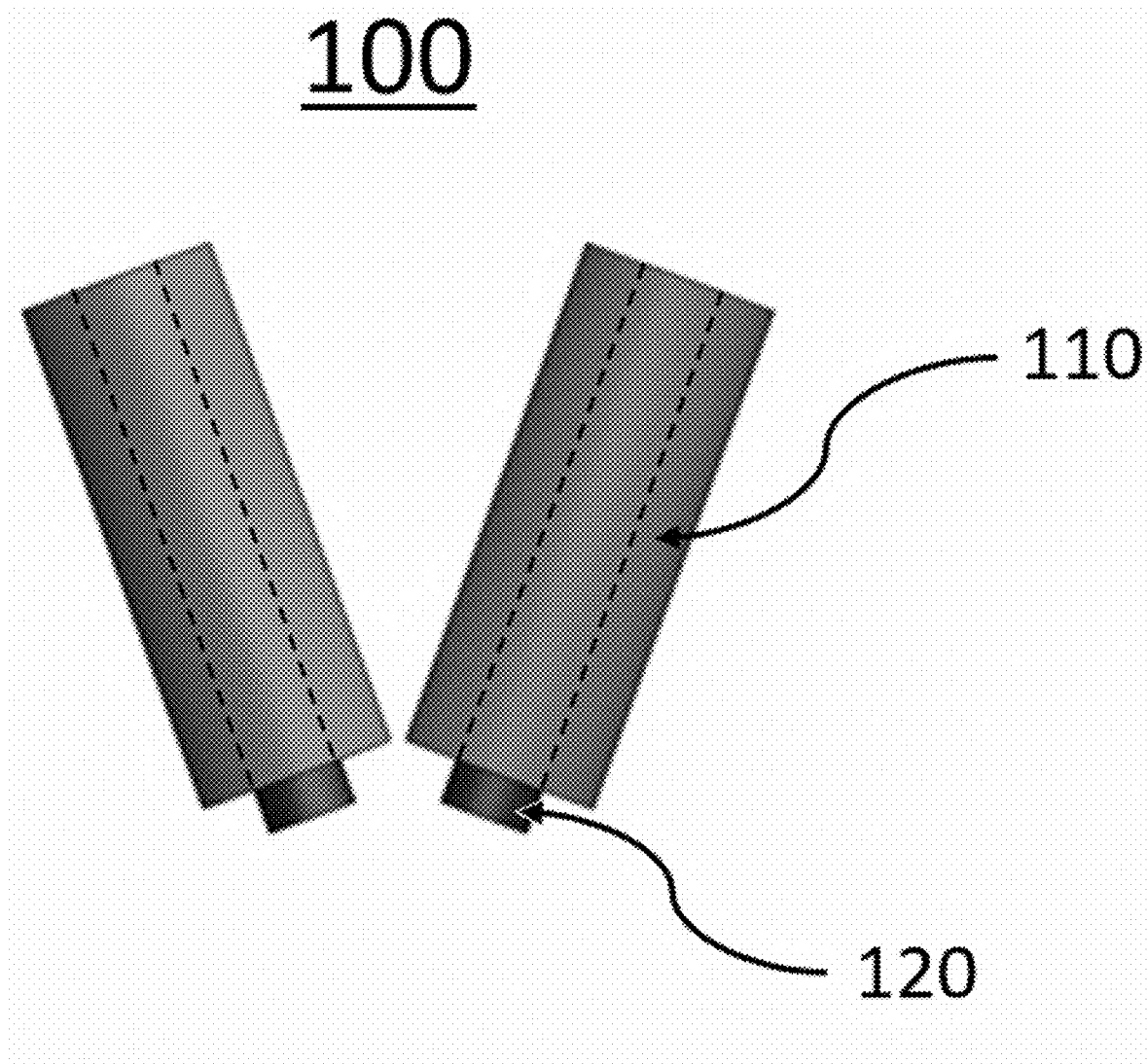
FIG. 1 is a diagram illustrating the configuration of an electromagnetic module according to an embodiment of the present disclosure.

An electromagnetic module for focusing a magnetic field may include two electromagnetic modules including a magnetic core configured as a paramagnet and a solenoid coil wound around the magnetic core, wherein the two electromagnetic modules are disposed to be symmetrical with each other with respect to an imaginary symmetric axis passing through the center of an area of interest, where the magnetic field is desired to be focused, on a two-dimensional plane including the symmetric axis.

DETAILED DESCRIPTION

Hereinafter, a detailed description of a preferred embodiment of the present disclosure will be described with reference to the accompanying drawings. In the following description of the present disclosure, if it is determined that a detailed description of a related known function or configuration may unnecessarily obscure the subject matter of the present disclosure, a detailed description thereof will be omitted.

Since embodiments according to the concept of the present disclosure may be modified in various ways, and may have various forms, specific embodiments will be illustrated in the drawings, and will be described in detail in the present specification or application. However, this is not intended to limit the embodiments according to the concept of the present disclosure to a specific form of disclosure, and should be understood to encompass all changes, equivalents, and substitutes included in the spirit and scope of the present disclosure.

In the case where one element is expressed as being "coupled" or "connected" to the other element, it must be understood that another element may be interposed between the two elements, as well as that one element may be directly coupled or connected to the other element.

On the other hand, in the case where one element is expressed as being "directly coupled" or "directly connected" to the other element, it must be understood that there is no other element therebetween. Other expressions indicating the relationship between elements, such as "between" and "just between" or "adjacent to" and "directly adjacent to" must be interpreted in the same manner.

The terms used in the present specification are only used to describe specific embodiments, and are not intended to limit the present disclosure. Singular expressions encompass plural expressions unless the context clearly indicates otherwise. In the present specification, terms such as "include" or "have" are intended to specify the presence of disclosed features, numbers, steps, operations, elements, components, or combinations thereof, and must be understood to not exclude the presence of one or more other features, numbers, steps, operations, elements, components, combinations thereof, or the possibility of supplement.

FIG. 1 is a diagram illustrating the configuration of an electromagnetic module 100 according to an embodiment of the present disclosure.

FIG. 1 illustrates a magnetic core 120 made of a paramagnet and a solenoid coil 110 wound around the magnetic core, which constitute each of two electromagnetic modules included in the electromagnetic module according to an embodiment of the present disclosure.

Figure 2:
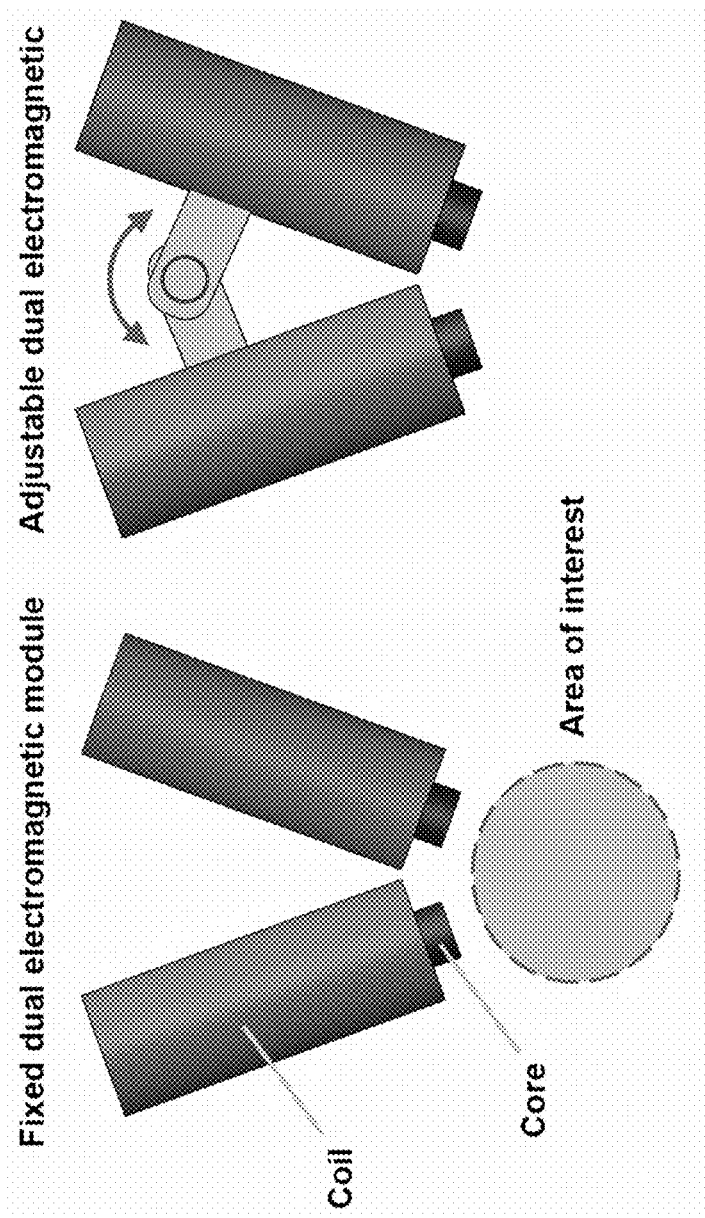
FIG. 2 is a diagram illustrating the configuration of an angle-fixed electromagnetic module and an angle-adjustable electromagnetic module according to an embodiment of the present disclosure.

FIG. 2 is a diagram illustrating the configuration of a "fixed dual electromagnetic module" in which two electromagnetic modules included in the electromagnetic module according to an embodiment of the present disclosure are disposed at a fixed angle and an "adjustable dual electromagnetic module" in which two electromagnetic modules are disposed at an adjustable angle.

The left diagram in FIG. 2 shows an area of interest where a magnetic field is desired to be focused by the electromagnetic modules. As shown in the drawing, two electromagnetic modules are disposed to be symmetrical with each other with respect to an imaginary symmetric axis passing through the center of the area of interest, where a magnetic field is desired to be focused, on a two-dimensional plane including the symmetric axis. This means that it is not a twisted arrangement structure that deviates from the two-dimensional plane.

The magnetic fields may be focused on the area where the magnetic fields formed by the respective electromagnetic modules overlap. The location of the electromagnetic module may be controlled such that the magnetic field is focused within the area of interest. Specifically, in the case of the "fixed electromagnetic module", the location of the magnetic field focus area may be controlled by three-dimensional spatial movement of the electromagnetic module and adjustment of the direction of the electromagnetic module, and in the case of the "adjustable electromagnetic module", the location of the magnetic field focus area may be controlled by adjusting the arrangement angle of two electromagnets, as well as three-dimensional spatial movement of the electromagnetic module and adjustment of the direction of the electromagnetic module.

Figure 3A:
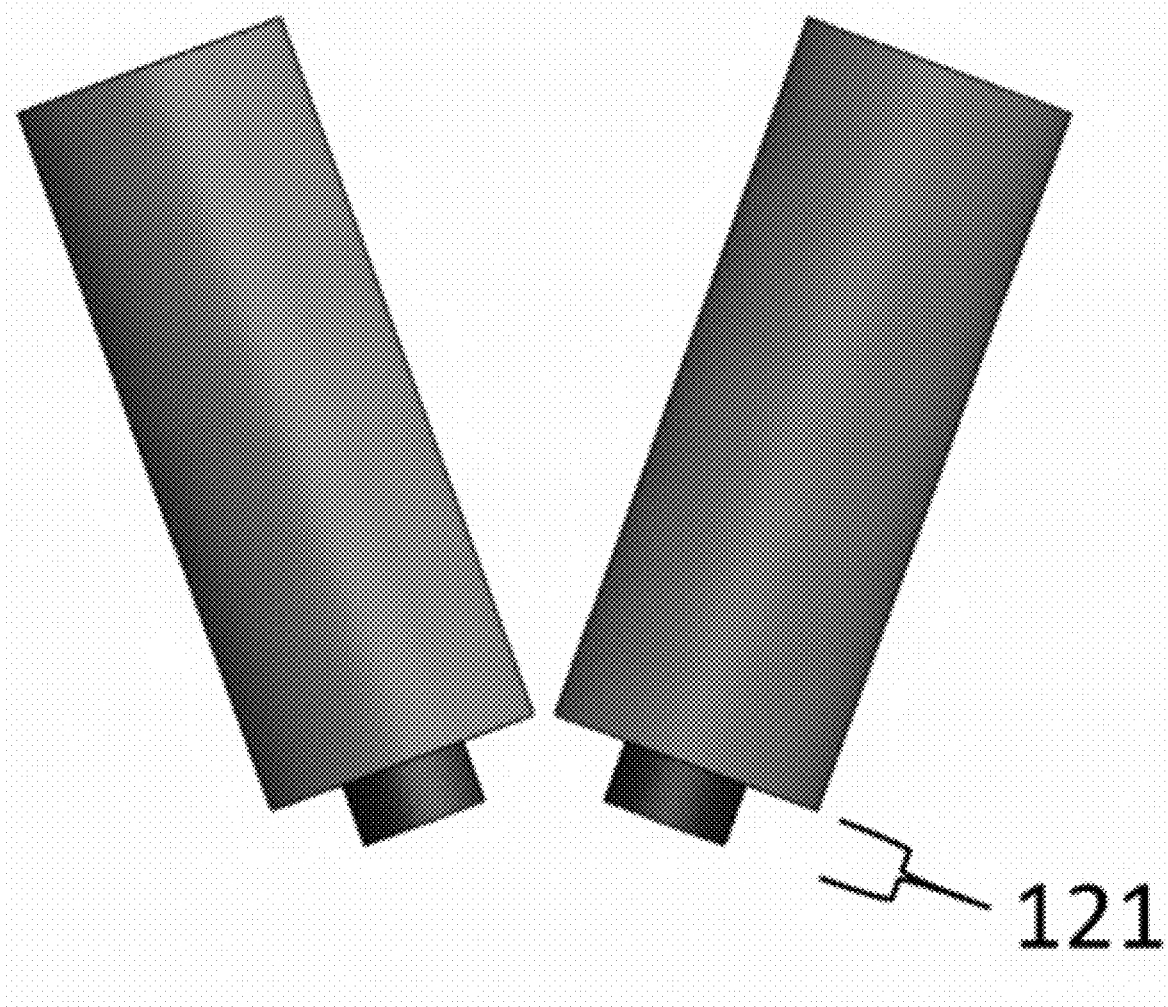
FIG. 3A is a diagram illustrating a basic form of various application examples of an electromagnetic module according to an embodiment of the present disclosure.

FIG. 3A illustrates a basic form of various application examples of an electromagnetic module, and a core may include a core protrusion 121 that is not wound.

Figure 3B:
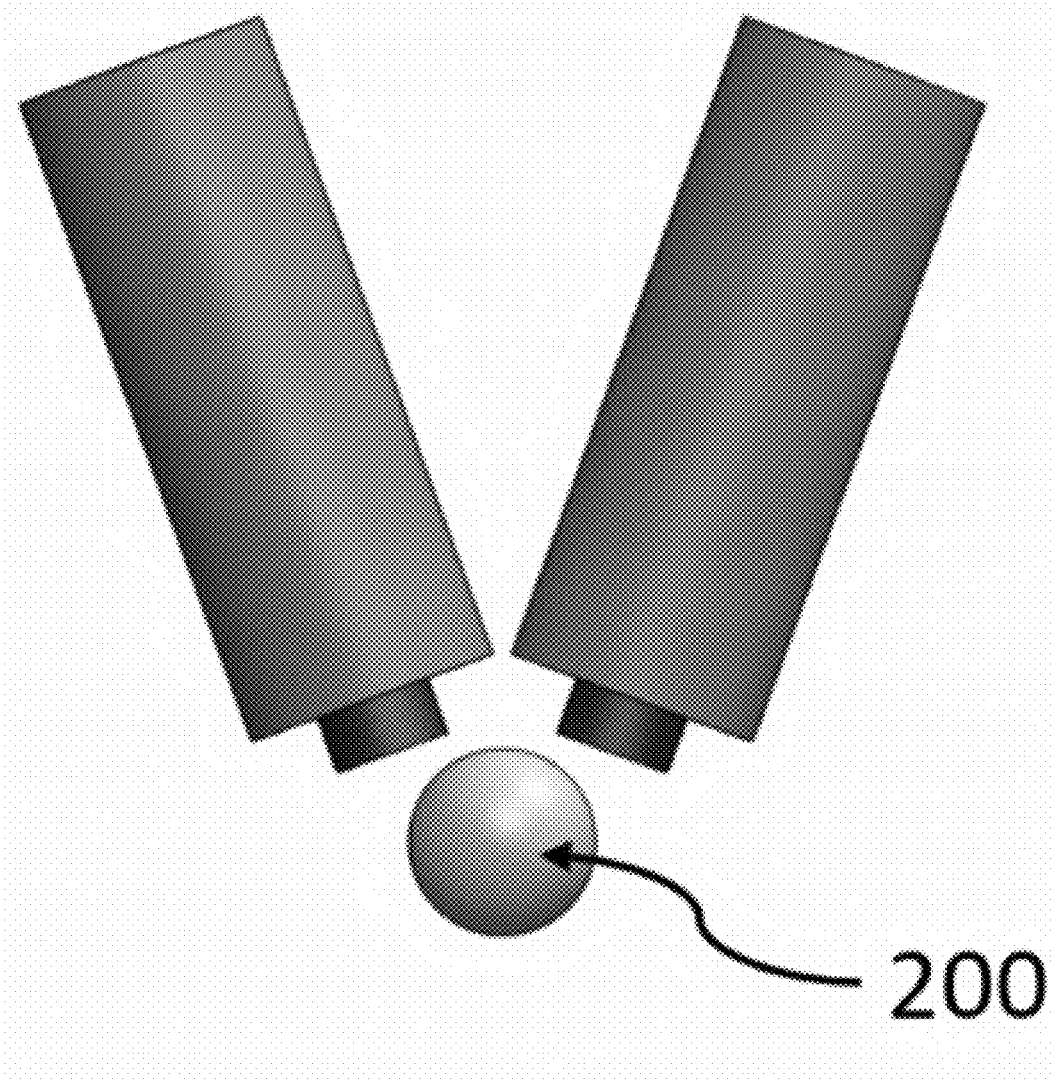
FIG. 3B is a diagram illustrating a rotation type core including a rotatable spherical paramagnet among various application examples of an electromagnetic module according to an embodiment of the present disclosure.
Figure 3C:
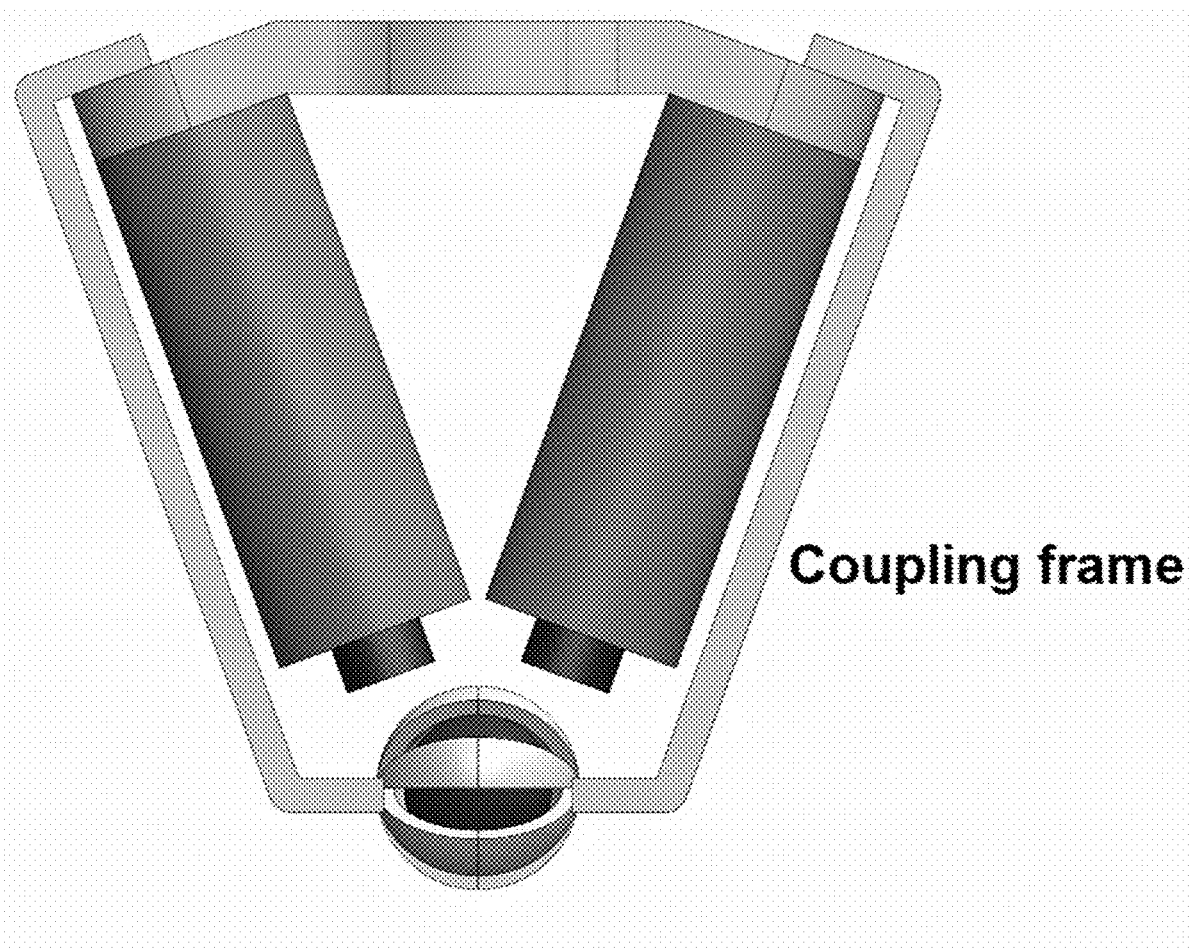
FIG. 3C is a diagram illustrating the state in which a coupling frame is coupled to a rotation type core including a rotatable spherical paramagnet among various application examples of an electromagnetic module according to an embodiment of the present disclosure.
Figure 3D:
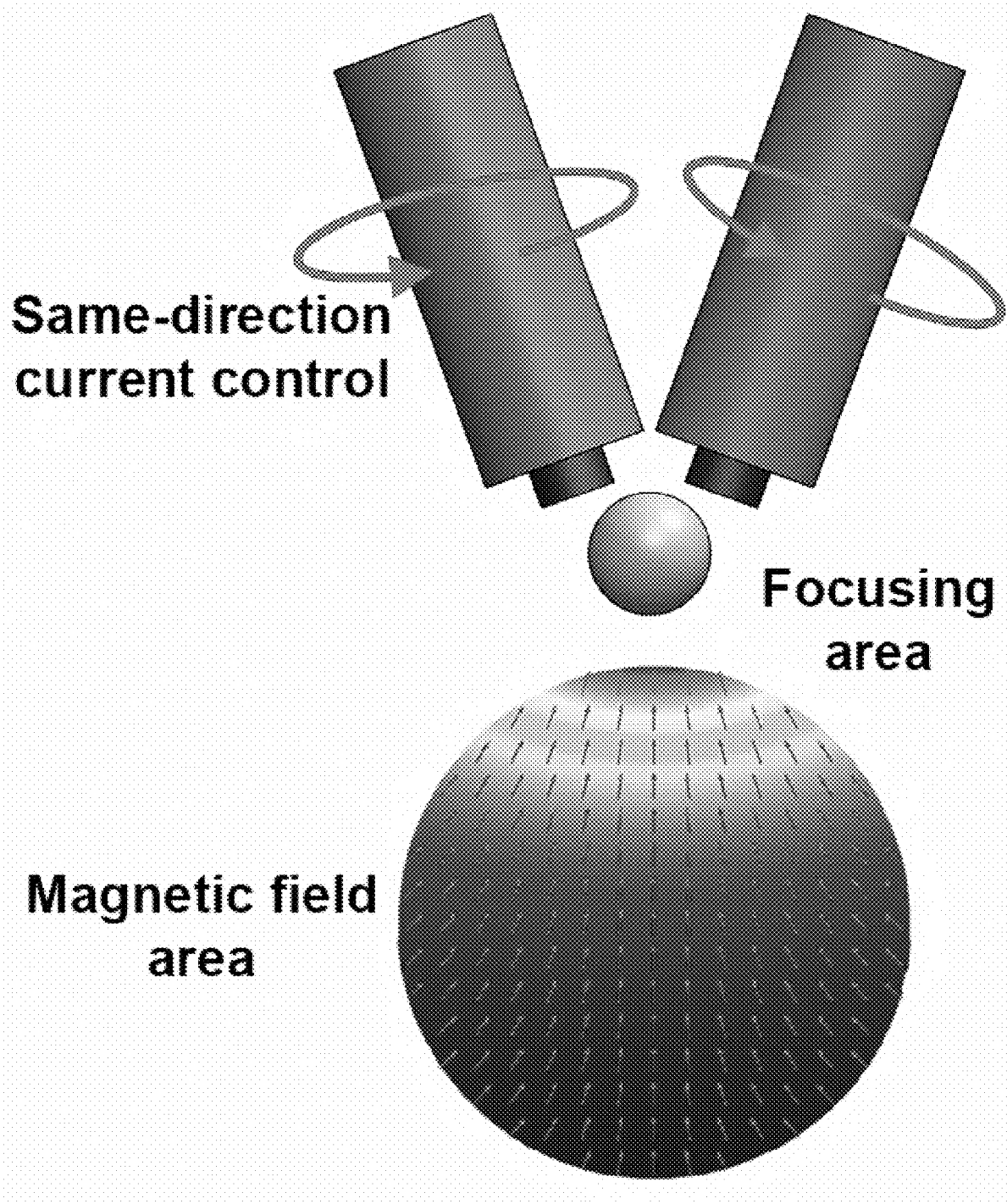
FIG. 3D is a diagram illustrating simulation of a magnetic field formed by same-direction current control in a rotation type core including a rotatable spherical paramagnet among various application examples of an electromagnetic module according to an embodiment of the present disclosure.
Figure 3E:
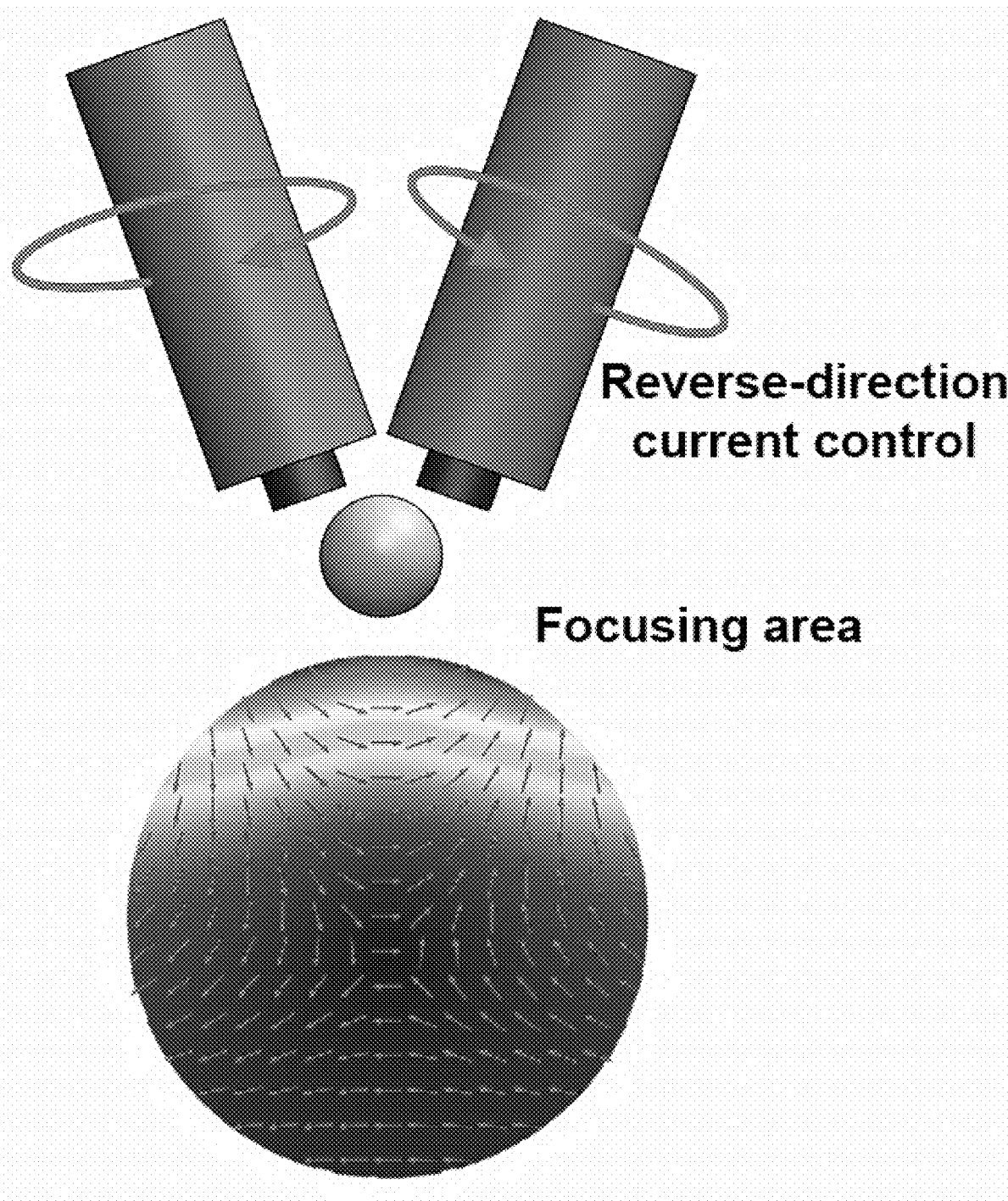
FIG. 3E is a diagram illustrating simulation of a magnetic field formed by reverse-direction current control in a rotation type core including a rotatable spherical paramagnet among various application examples of an electromagnetic module according to an embodiment of the present disclosure.

FIG. 3B illustrates an example of a dual electromagnetic module including a rotatable spherical paramagnet. FIG. 3C is a diagram illustrating the state in which a coupling frame is coupled to a rotation type core including a rotatable spherical paramagnet among various application examples of a dual electromagnetic module, FIG. 3D is a diagram illustrating simulation of a magnetic field formed by same-direction current control thereof, FIG. 3E is a diagram illustrating simulation of a magnetic field formed by reverse-direction current control.

Figure 3F:
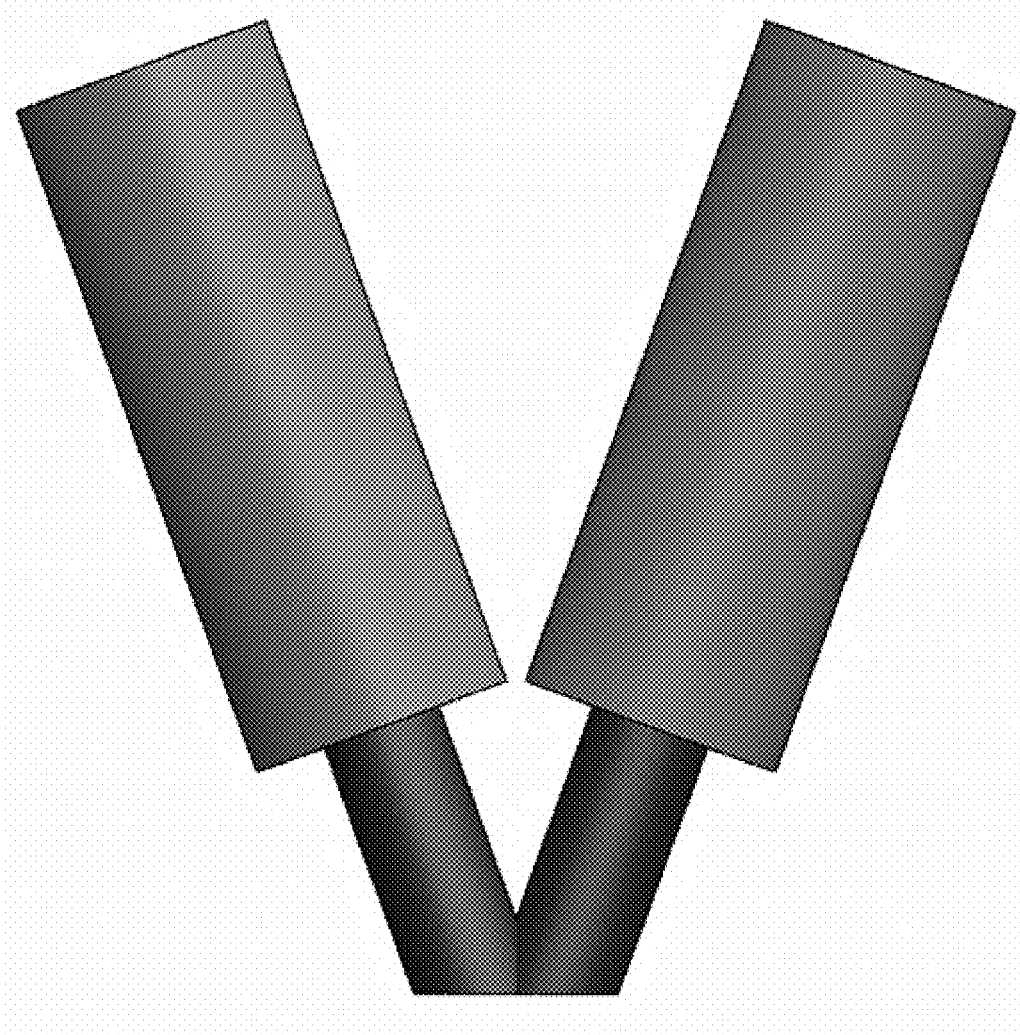
FIG. 3F is a diagram illustrating contact type cores in which core protrusions are disposed adjacent to each other among various application examples of an electromagnetic module according to an embodiment of the present disclosure.
Figure 3G:
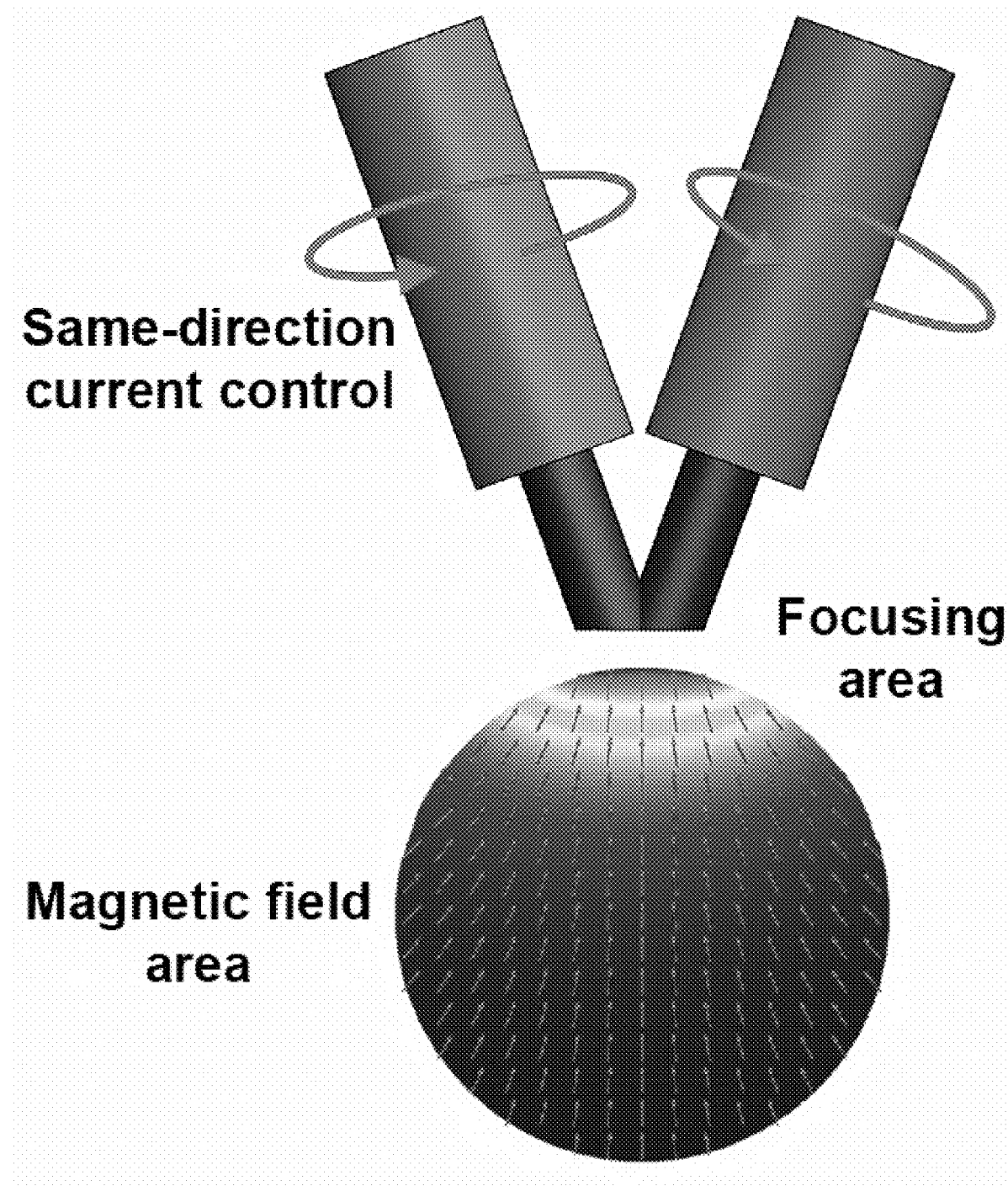
FIG. 3G is a diagram illustrating simulation of a magnetic field formed by same-direction current control in contact type cores in which core protrusions are disposed adjacent to each other among various application examples of an electromagnetic module according to an embodiment of the present disclosure.
Figure 3H:
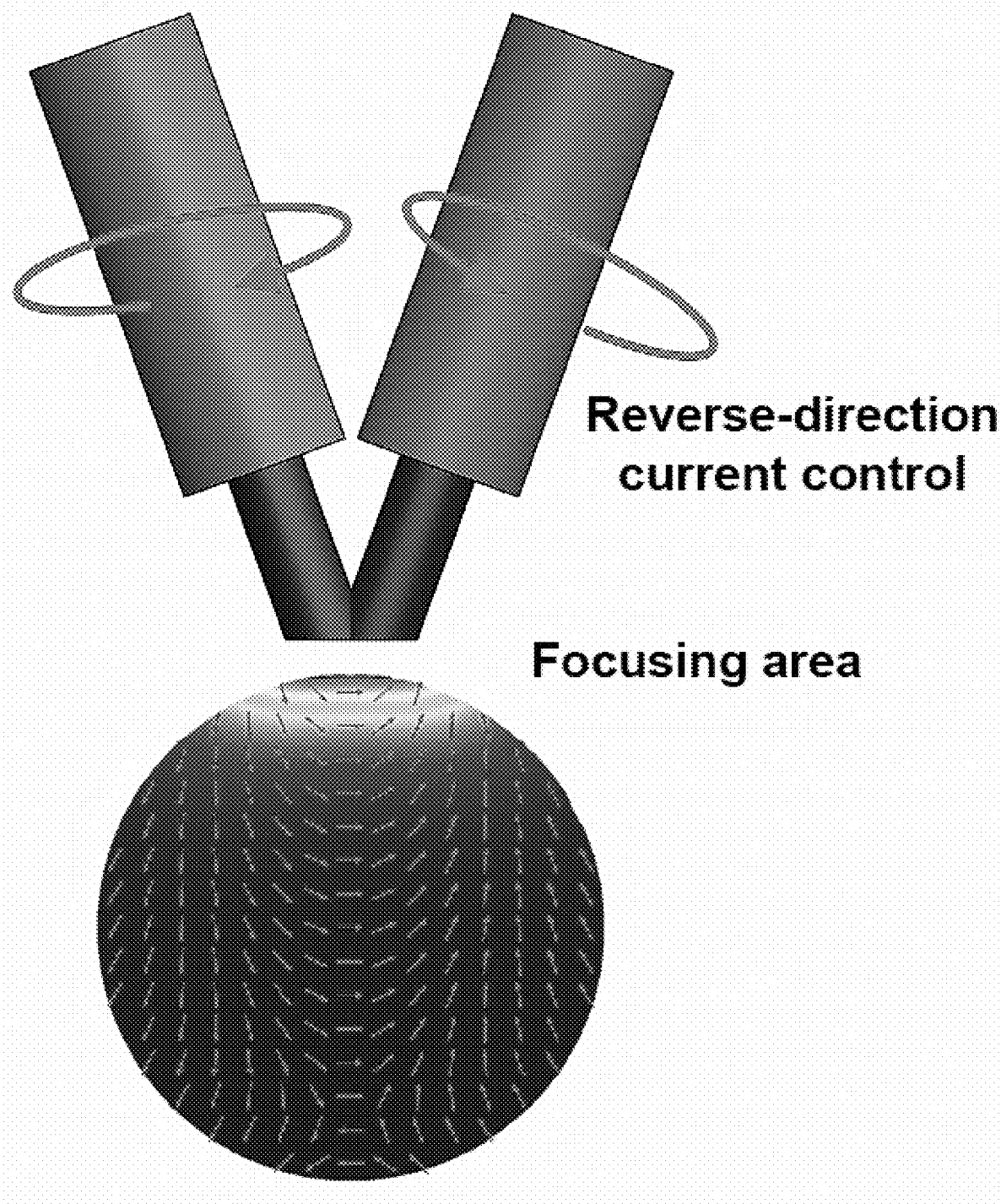
FIG. 3H is a diagram illustrating simulation of a magnetic field formed by reverse-direction current control in contact type cores in which core protrusions are disposed adjacent to each other among various application examples of an electromagnetic module according to an embodiment of the present disclosure.

FIG. 3F illustrates an electromagnetic module in which core protrusions are disposed adjacent to each other. FIG. 3G is a diagram illustrating simulation of a magnetic field formed by same-direction current control in a contact type core in which core protrusions are disposed adjacent to each other, and FIG. 3H is a diagram illustrating simulation of a magnetic field formed by reverse-direction current control.

Figure 4A:
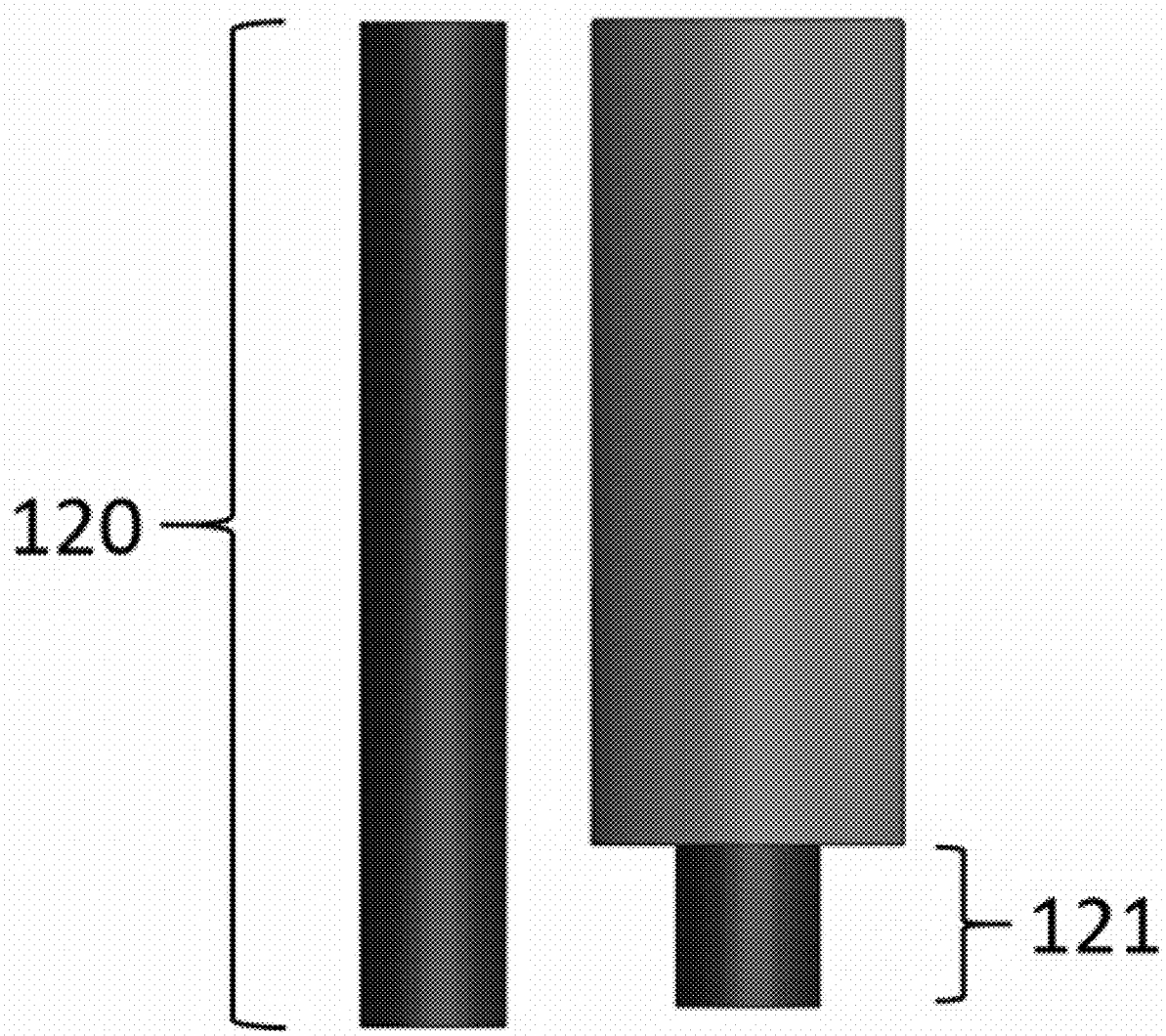
FIG. 4A illustrates an example of a dual electromagnetic module having a basic core protrusion in a cylindrical shape among examples including various shapes of core protrusions according to an embodiment of the present disclosure.
Figure 4B:
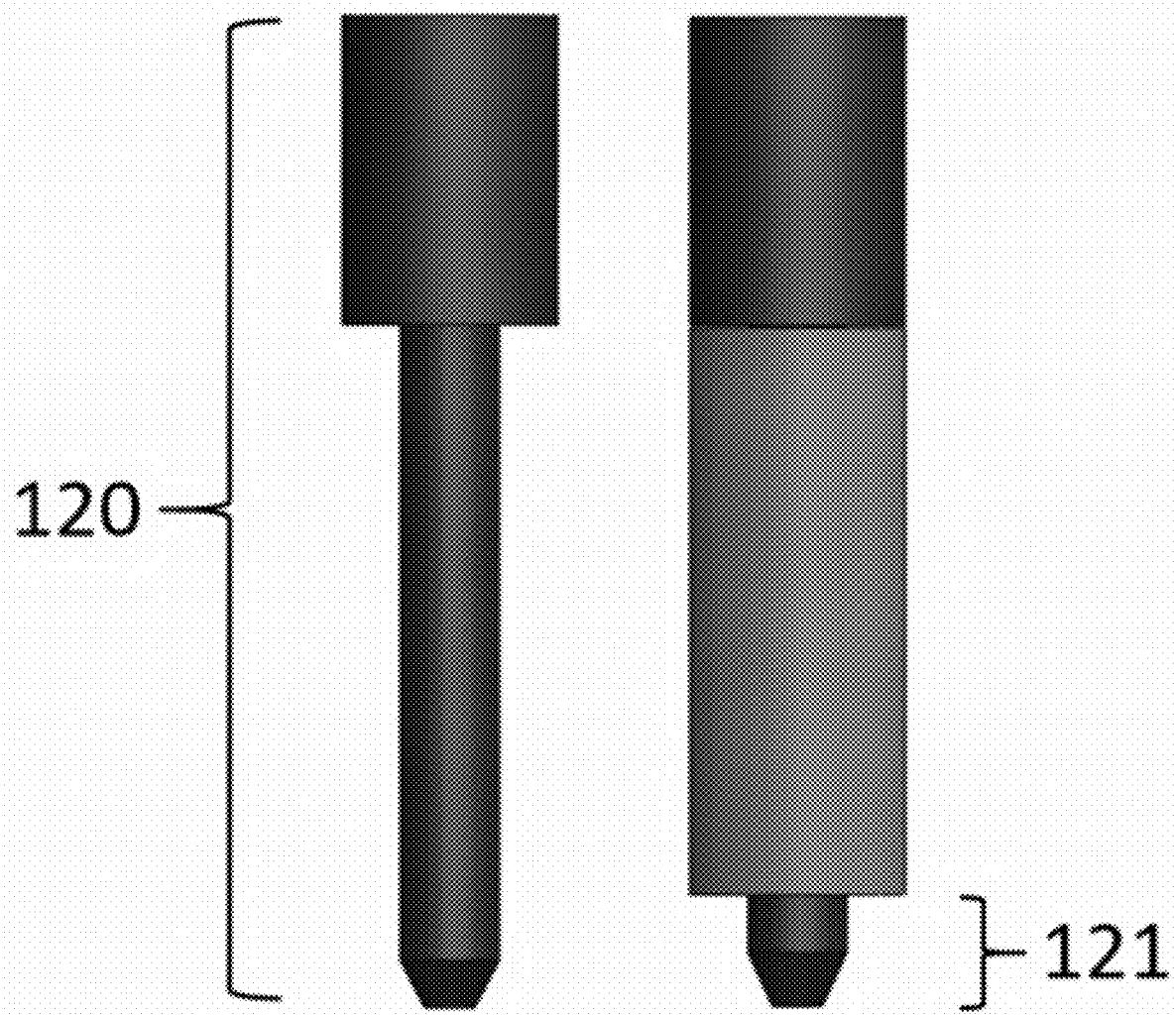
FIG. 4B illustrates an example of a magnetic field focus type electromagnetic module including a core protrusion whose end is gradually narrowed among examples including various shapes of core protrusions according to an embodiment of the present disclosure.
Figure 4C:
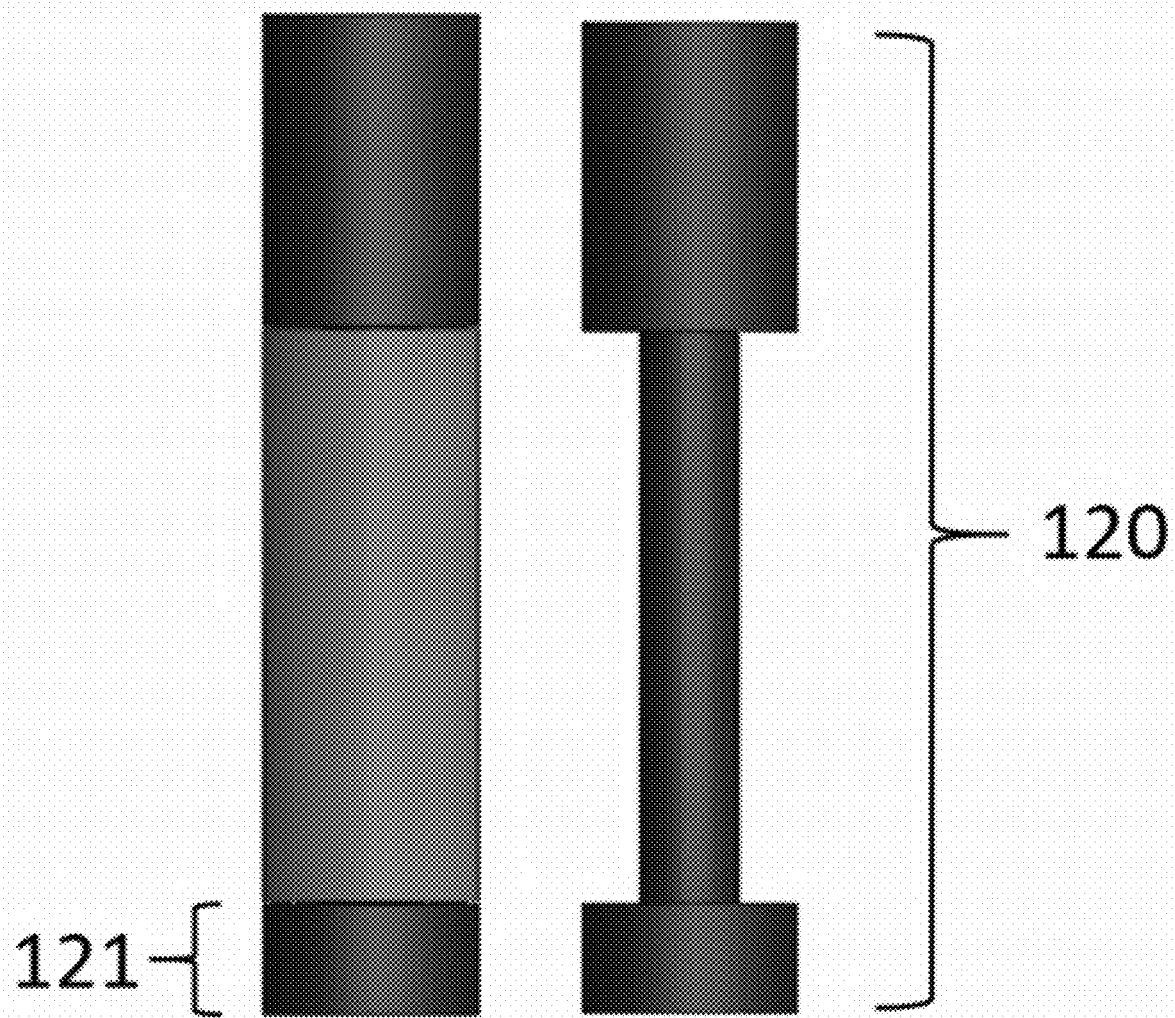
FIG. 4C illustrates an example of a uniform-magnetic field extension type electromagnetic module including a core protrusion having a diameter equal to the outer diameter of a solenoid coil among examples including various shapes of core protrusions according to an embodiment of the present disclosure.

FIGS. 4A to 4C illustrate the configuration of an embodiment including core protrusions in various shapes. FIG. 4A illustrates an example of an electromagnetic module having a basic core protrusion 121 in a cylindrical shape, and the core protrusion has a cylindrical shape having the same diameter as the inner diameter of a solenoid coil. FIG. 4B illustrates an example of a magnetic field focus type electromagnetic module including a core protrusion 121 whose end is gradually narrowed. Specifically, for example, in the core protrusion, the diameter of a portion at which a protrusion starts may be the same as the inner diameter of the solenoid coil, and the diameter of the end of the core protrusion may be smaller than the inner diameter of the solenoid coil. More specifically, for example, the core protrusion may have a shape of a truncated cone or a combination of a cylinder and a truncated cone. In the case of using the magnetic field focus type electromagnetic module having the core protrusion in which the end thereof is gradually narrowed as described above, it is possible to realize a magnetic field focused on a narrow area with a higher density.

FIG. 4C illustrates an example of a uniform-magnetic field extension type dual electromagnetic module including a core protrusion 121 having the same diameter as the outer diameter of a solenoid coil. In the case of using a magnetic field focus type dual electromagnetic module including a core protrusion having the same diameter as the outer diameter of the solenoid coil as described in the present embodiment, it is possible to implement a wider magnetic field area with uniform intensity.

Figure 5A:
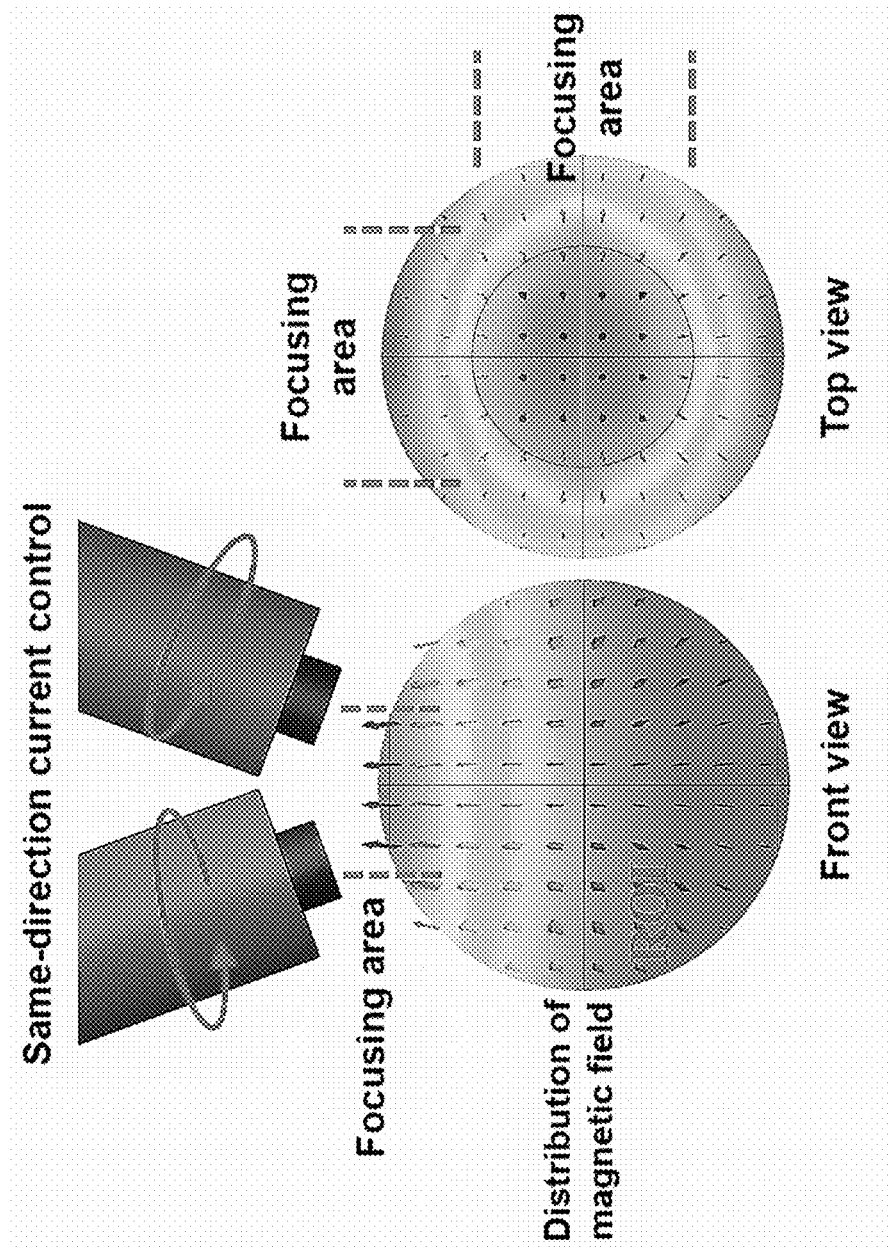
FIG. 5A is a simulation diagram illustrating the area of a magnetic field generated when current flows in the same rotational direction through respective solenoid coils of an electromagnetic module according to an embodiment of the present disclosure.
Figure 5B:
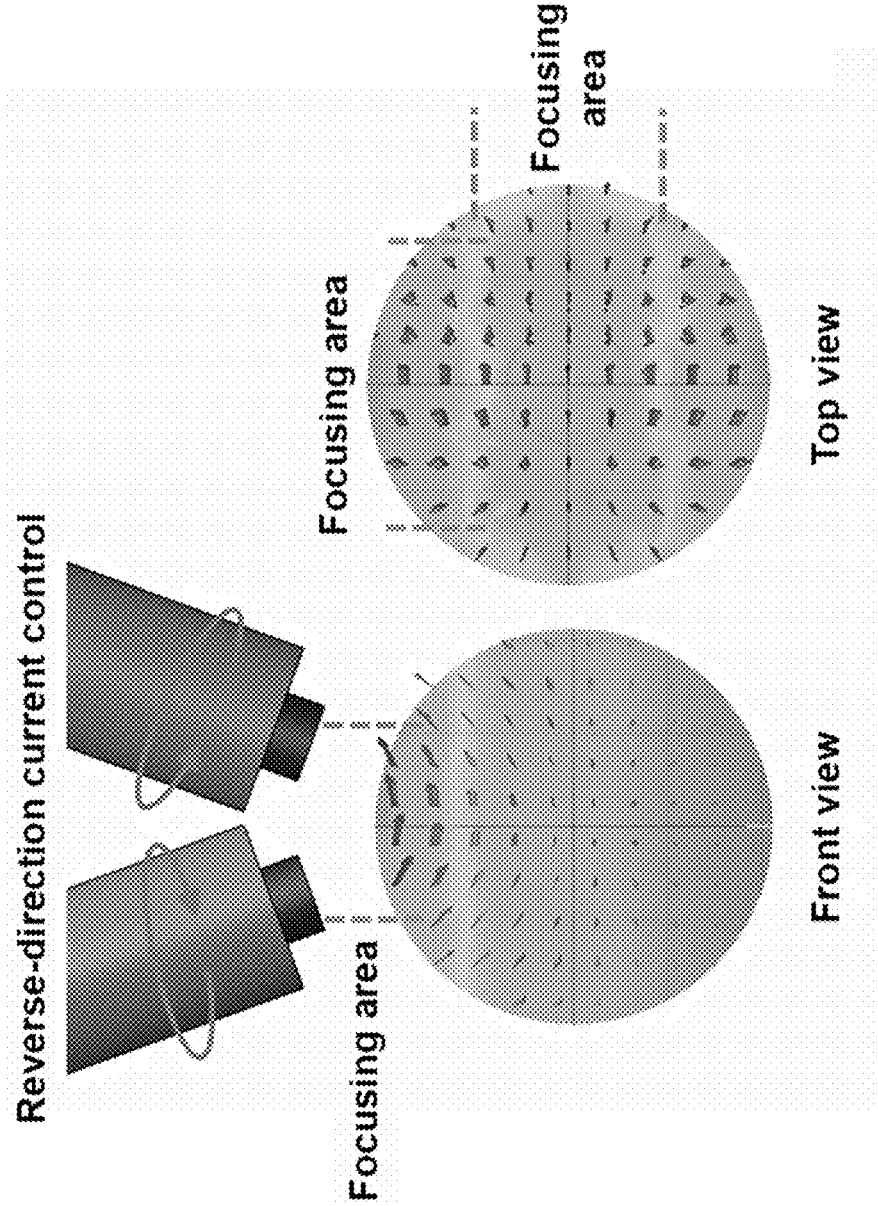
FIG. 5B is a simulation diagram illustrating the area of a magnetic field generated when current flows in the opposite rotational directions through respective solenoid coils of each electromagnetic module according to an embodiment of the present disclosure.

FIGS. 5A and 5B illustrate simulation of a magnetic field area formed depending on the direction of current flowing through a pair of solenoid coils. In the case where current flows through the solenoid coils of the two electromagnetic modules in the same rotational direction, the magnetic field may be focused in a circular shape at the center of an upper portion as shown in the top view of FIG. 5A. In the case where current flows through the solenoid coils of the two electromagnetic modules in the opposite rotational directions, the magnetic field may be focused in an elliptical shape at the center of an upper portion as shown in the top view of FIG. 5B.

A micro-robot control apparatus according to another aspect of the present disclosure is characterized by including the above-described electromagnetic modules; a power source configured to supply power to the solenoid coils of the electromagnetic modules; and a moving part configured to control a rotational motion of the electromagnetic modules with respect to the symmetric axis and a three-dimensional linear motion thereof.

Figure 6:
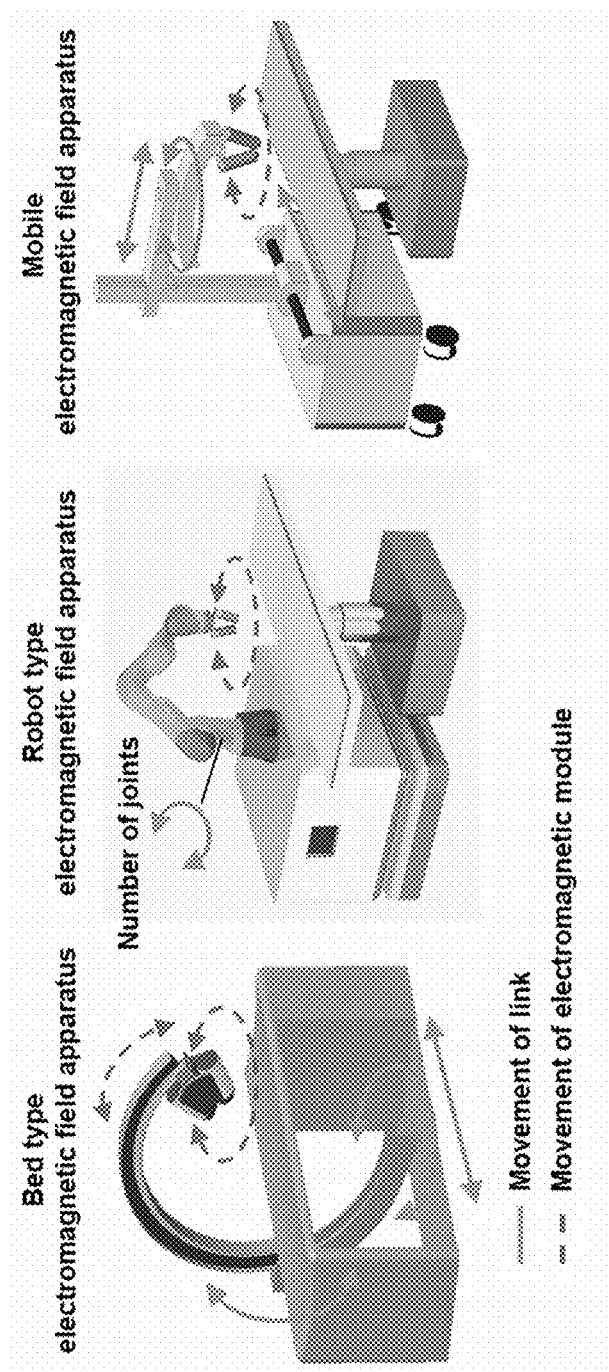
FIG. 6 illustrates embodiments of a micro-robot control apparatus equipped with an electromagnetic module according to an embodiment of the present disclosure.

FIG. 6 illustrates embodiments of a micro-robot control apparatus having an electromagnetic module. A micro-robot control apparatus according to embodiments of the present disclosure includes a link that is a moving part configured to control the movement of a dual electromagnetic module, which is obtained by coupling electromagnetic modules, in a three-dimensional space, and any conventional method may be employed as the shape or driving method of the link, which is not limited to a specific form. The link according to an embodiment of the present disclosure may have the shape of a circular arc that is located on the plane perpendicular to the longitudinal axis of a bed (see the left view in FIG. 6), and the link may operate to move linearly along the longitudinal axis of the bed and rotate around the longitudinal axis of the bed. In addition, the link according to another embodiment of the present disclosure may have the shape of a robot arm provided with one or two or more joints (see the middle view in FIG. 6), and the link may operate to control the movement of the electromagnetic module in the three-dimensional space by the rotational motion of the joints. In addition, the link according to another embodiment of the present disclosure may be configured to include a linear y-axis guide rod disposed in a direction perpendicular to the plane of the bed on which a patient lies and an x-axis guide rod connected to the y-axis guide rod in a direction perpendicular thereto, thereby enabling longitudinal extension and/or the locational movement of the contact, and a dual electromagnetic module according to an embodiment of the present disclosure may be coupled to one end of the x-axis guide rod so as to move the dual electromagnetic module by a change in the lengths and/or locations of the y-axis guide rod and the x-axis guide rod. Additionally, the dual electromagnetic module may be directly connected to the x-axis guide rod, or may be connected to one end of a rotating guide rod that is connected to one end of the x-axis guide rod and serves as a linker capable of rotational motion.

The power source for supplying power to the solenoid coil of the electromagnetic module according to an embodiment of the present disclosure may include two power supplies connected to two electromagnetic modules of the dual electromagnetic module, respectively, or may include a power supply having one or two output channels. Preferably, in order to apply current in the same or opposite directions to the two electromagnetic modules included in the electromagnetic module, two power supplies may be included, or a power supply having two output channels may be used.

Figure 7A:
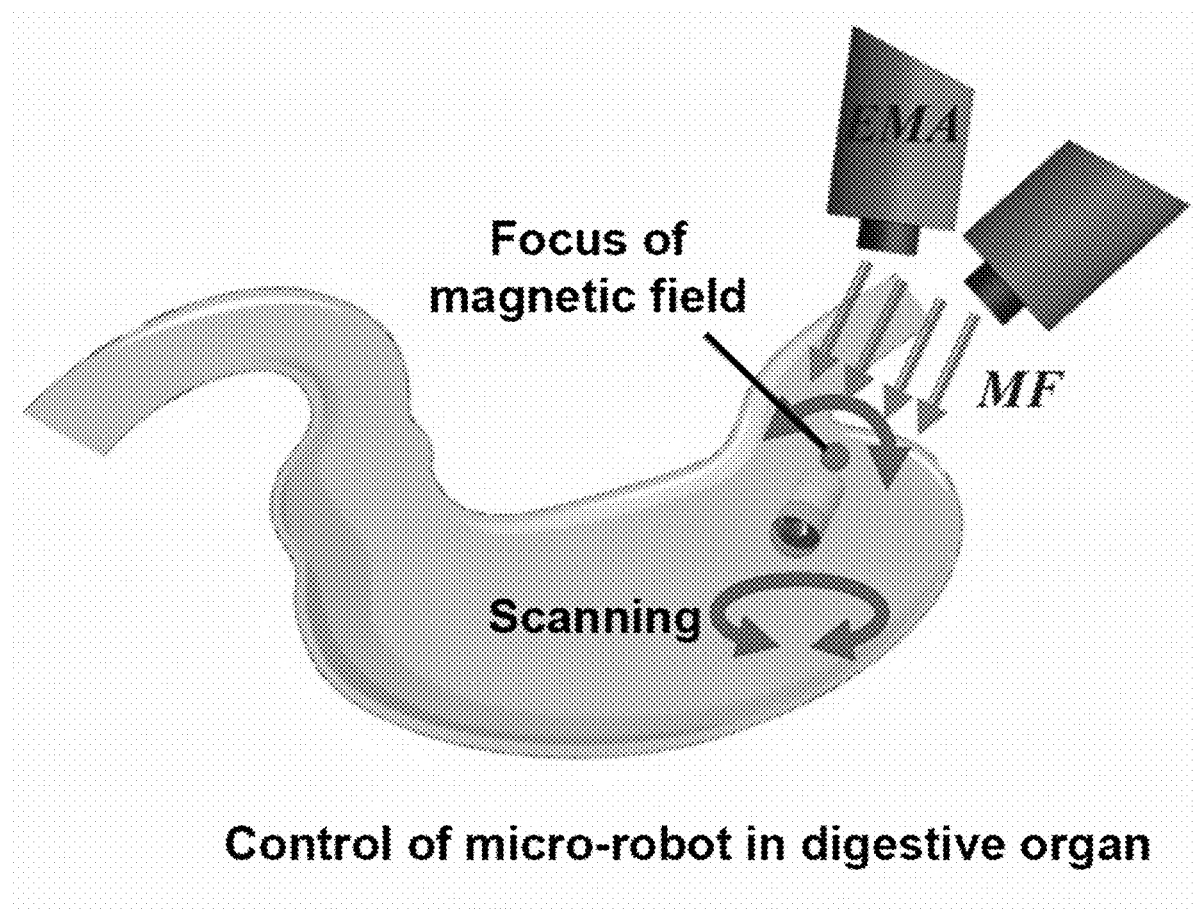
FIG. 7A is a conceptual diagram illustrating a method of controlling the driving of a micro endoscope robot including an image capturing unit inside a digestive organ by the operation of an electromagnetic module according to an embodiment of the present disclosure.
Figure 7B:
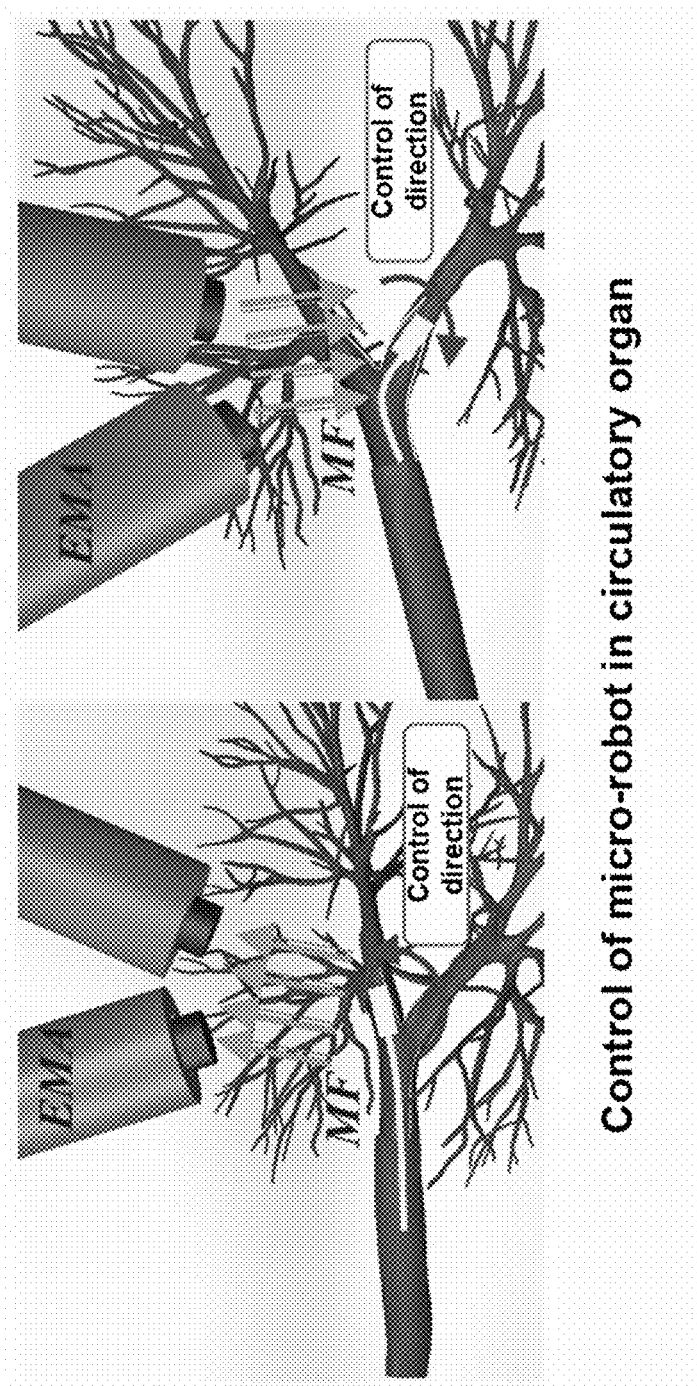
FIG. 7B is a conceptual diagram illustrating a method of controlling the driving of a micro-robot in a blood vessel, which is a circulatory organ, by the operation of an electromagnetic module according to an embodiment of the present disclosure.

FIG. 7 is a conceptual diagram illustrating a method of controlling the driving of a micro-robot in the human body by the operation of electromagnetic modules. FIG. 7A illustrates an embodiment of driving a micro-robot inside a digestive organ, specifically, for example, a capsule endoscope robot including an image capturing unit. Using the electromagnetic module according to an embodiment of the present disclosure, it is possible to focus a magnetic field on a certain location inside the digestive organ. By controlling the direction of the current applied to the electromagnetic module or by controlling the rotational motion of the electromagnetic module, it is possible to freely control the rotational motion of the micro-robot located inside the digestive organ, specifically, for example, the capsule endoscope robot, and to further control the movement of various micro-robots for various purposes, as well as the capsule endoscope robot. FIG. 7B illustrates an embodiment of driving a micro-robot in a circulatory organ, specifically, for example, a blood vessel. In the case of using the electromagnetic module according to an embodiment of the present disclosure, it is possible to freely control the movement of the micro-robot in the blood vessel, and, in particular, to freely control the path of the micro-robot at a contact point where several blood vessels extend.

Figure 8A:
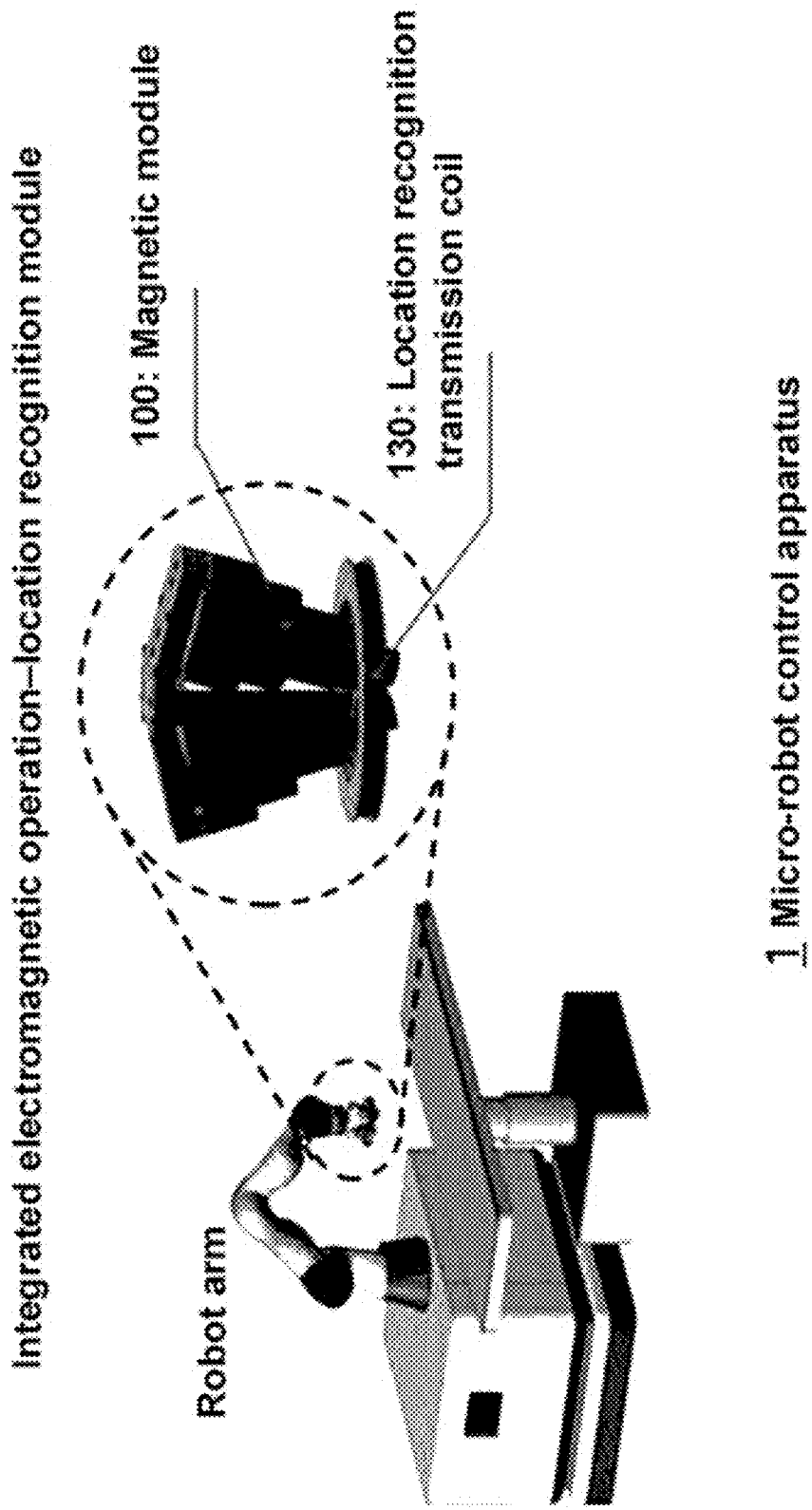
FIG. 8A schematically illustrates a micro-robot control apparatus equipped with two electromagnetic modules and a magnetic induction transmission coil for generating a magnetic induction frequency signal for recognizing the location of a micro-robot according to the present disclosure.
Figure 8B:
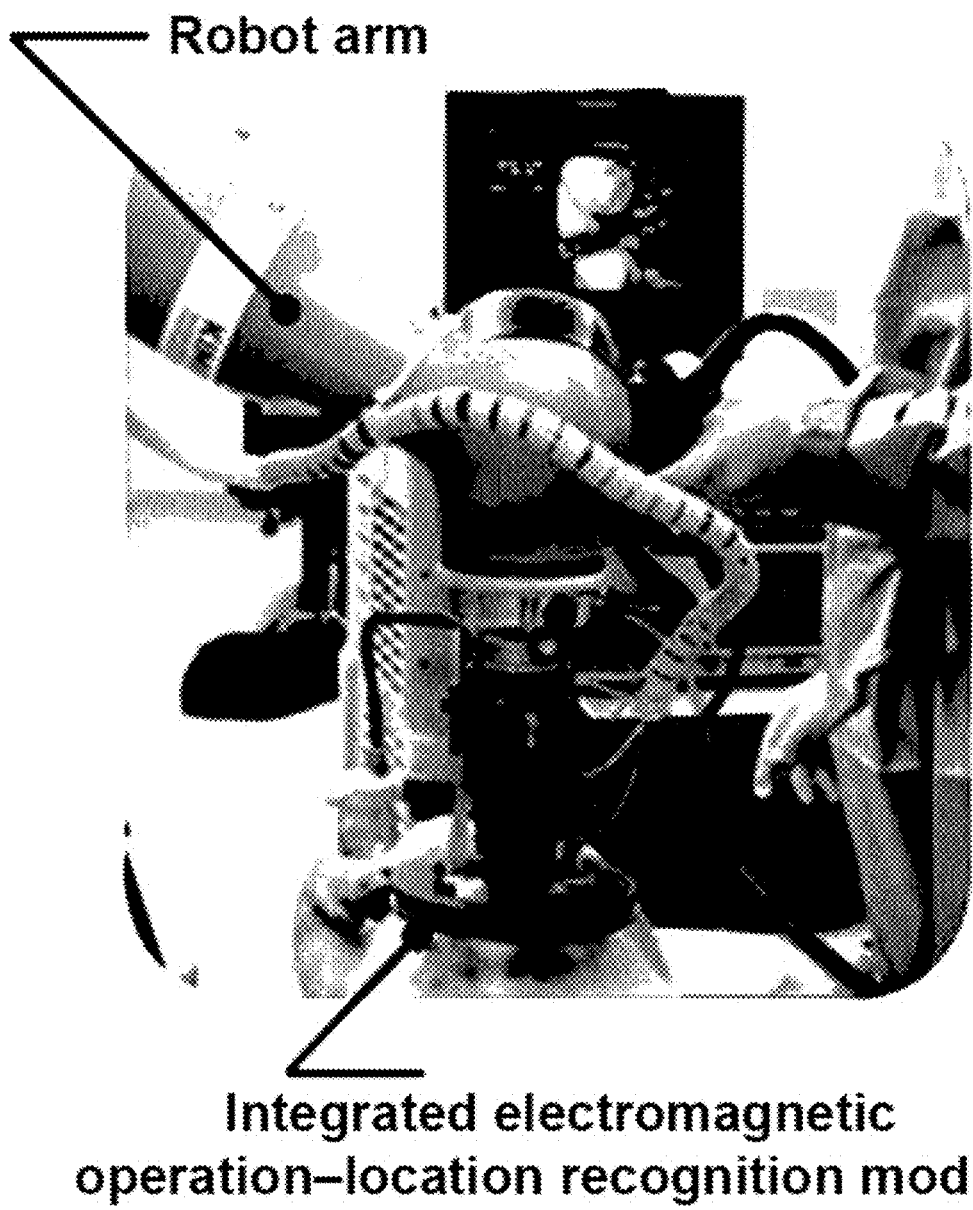
FIG. 8B illustrates a micro-robot control apparatus equipped with two electromagnetic modules and a magnetic induction transmission coil for generating a magnetic induction frequency signal for recognizing the location of a micro-robot according to the present disclosure.

FIGS. 8A and 8B illustrate a micro-robot control apparatus 1 equipped with two electromagnetic modules of the present disclosure and a magnetic induction transmission coil for generating a magnetic induction frequency signal for recognizing the location of a micro-robot according to the present disclosure.

As shown in FIG. 8, a Location recognition transmission coil 130 for generating a magnetic induction frequency signal for recognizing the location of a micro-robot may be provided at the location where the core protrusion 121 of the electromagnetic module is formed.

The driving of the micro-robot may be freely controlled by the electromagnetic module 100 provided in the micro-robot control apparatus 1 as described above, and the operation of recognizing the location of the micro-robot will be described in detail below.

The magnetic induction transmission coil 130 may be designed to generate an AC magnetic field of several mT in a band of several kHz and to cover the area of a digestive organ in the human body in which the capsule endoscope operates.

One or more magnetic induction transmission coils 130 may be coupled in an electromagnetic driving device (this indicates, for example, an electromagnetic module of the present disclosure) that generates an electromagnetic field among the micro-robot control apparatus, and the number of magnetic induction transmission coils 130 may be determined depending on the operation range of the micro-robot in the human body.

The inside of the human body may be observed through a micro-robot driven by a DC magnetic field generated by the electromagnetic driving device, and the location of the micro-robot may be recognized using a magnetic induction frequency signal generated by the magnetic induction transmission coil 130.

The micro-robot inserted into the human body may be configured in micro-units or nano-units, and one or more micro-robots may be inserted into the human body as necessary.

At this time, the micro-robot control apparatus may recognize the location of the micro-robot by receiving and analyzing the amount of electromotive force induced in the micro-robot through a magnetic induction frequency signal, and in particular, the location in 6 degrees of freedom (DOF) may be recognized in order to recognize the exact location inside the human body.

Figure 9:
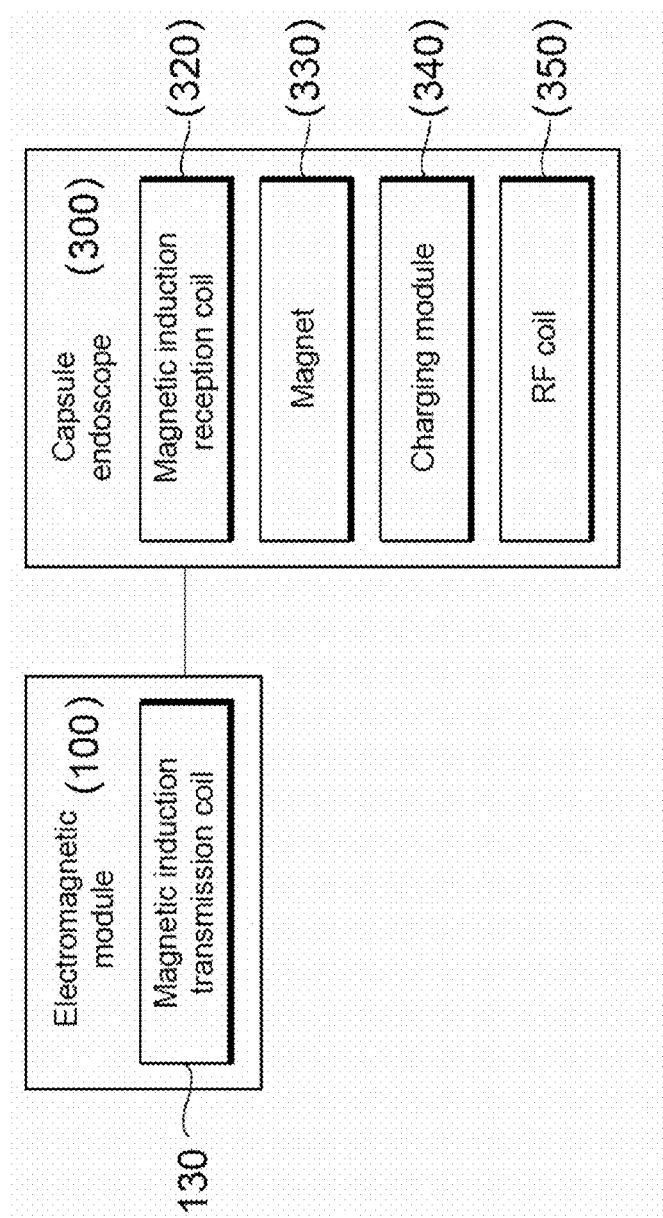
FIG. 9 is a block diagram schematically illustrating the configuration of a location recognition system of a capsule endoscope, which is a specific example of a micro-robot, in a micro-robot control apparatus according to the present disclosure.
Figure 10:
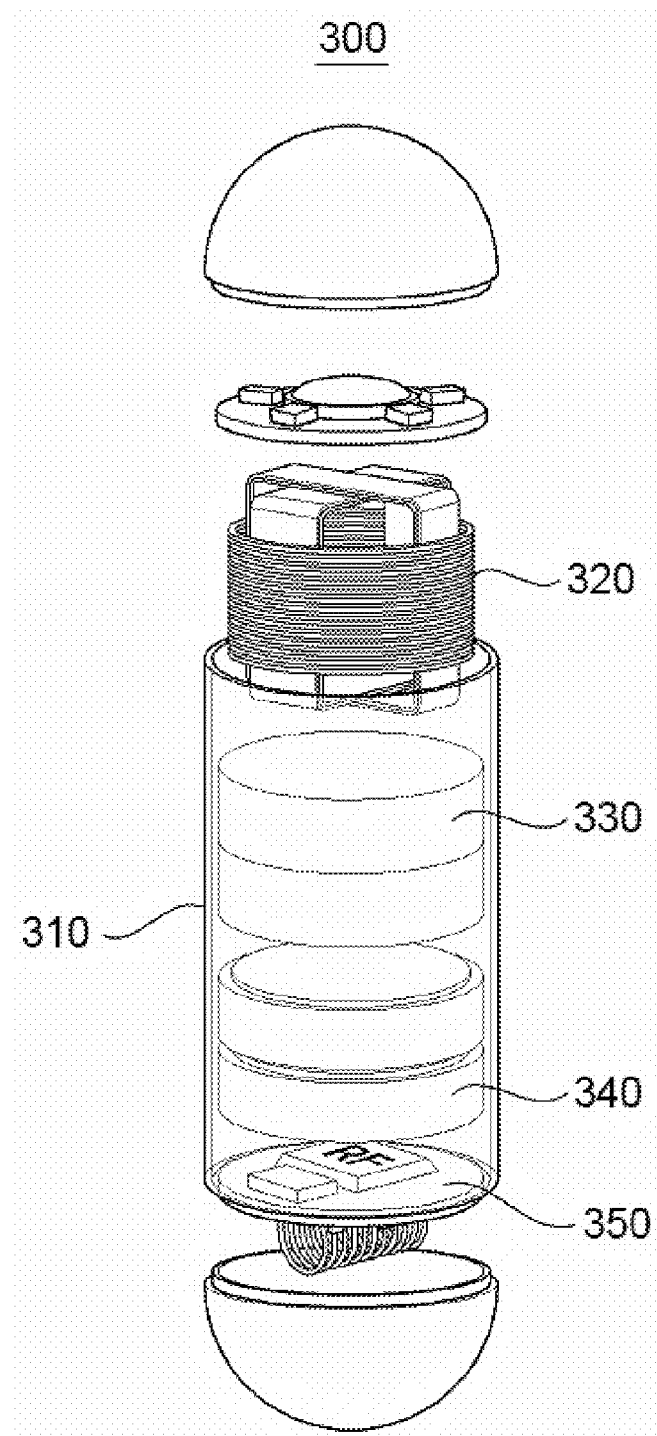
FIG. 10 is a diagram schematically illustrating a capsule endoscope, which is a specific example of a micro-robot, in a micro-robot control apparatus according to the present disclosure.

FIG. 9 schematically illustrates the configuration of a location recognition system of a capsule endoscope, which is a specific example of a micro-robot, in a micro-robot control apparatus according to the present disclosure, and FIG. 10 is illustrates the specific configuration of a capsule endoscope.

As shown in FIG. 10, a capsule endoscope 300 may include a body 310, a magnetic induction reception coil 320, a magnet 330, a charging module 340, and an RF (radio frequency) coil 350.

The body 310 constituting the capsule endoscope 300 is configured in the form of a capsule having a size of a micro-unit or nano-unit.

The magnetic induction reception coil 320 disposed inside the body 310 generates an electromotive force induced from a magnetic induction frequency signal applied from the magnetic induction transmission coil 130 of the micro-robot control apparatus 1.

The magnet 330 is magnetized in an arbitrary direction inside the body 310 for electromagnetic driving, and interacts with a DC magnetic field generated from the micro-robot control apparatus 1, thereby driving the capsule endoscope 300.

The charging module 340 may be charged using the electromotive force induced by the magnetic induction reception coil 320 in a wireless manner.

In addition, the RF (radio frequency) coil 350 transmits the induced power generated from the magnetic induction reception coil 320, that is, a frequency signal of the electromotive force for charging the charging module 340, to the micro-robot control apparatus 1.

Therefore, the external micro-robot control apparatus 1 may recognize the location of the capsule endoscope 300 from the amount of electromotive force induced by the capsule endoscope 300.

Figure 11:
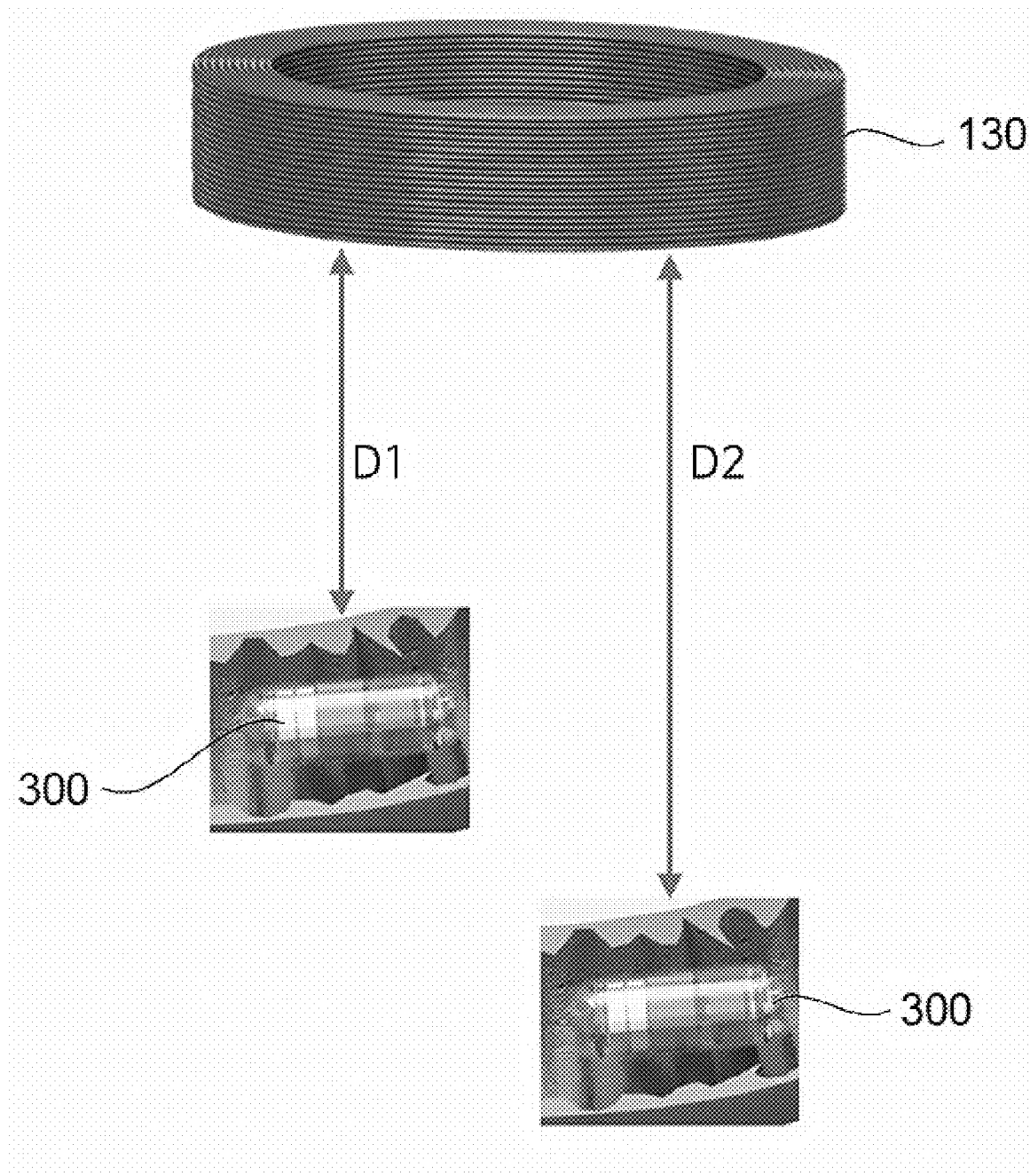
FIG. 11 is a diagram illustrating a relationship between a difference in the distance between a magnetic induction transmission coil and a capsule endoscope and power reception efficiency in a micro-robot control apparatus according to the present disclosure.

FIG. 11 is a diagram illustrating a relationship between a difference in the distance between a magnetic induction transmission coil and a capsule endoscope, and power reception efficiency, and the location may be recognized through the power reception efficiency generated depending on the difference in the distance between the magnetic induction transmission coil 130 of the micro-robot control apparatus 1 and the capsule endoscope 300. That is, the capsule endoscope 300, which is located at a distance D1 shorter than the distance D2, has high power reception efficiency from the magnetic induction transmission coil 130 so that the micro-robot control apparatus 1 may recognize the location of the capsule endoscope 300 according thereto.

Figure 12:
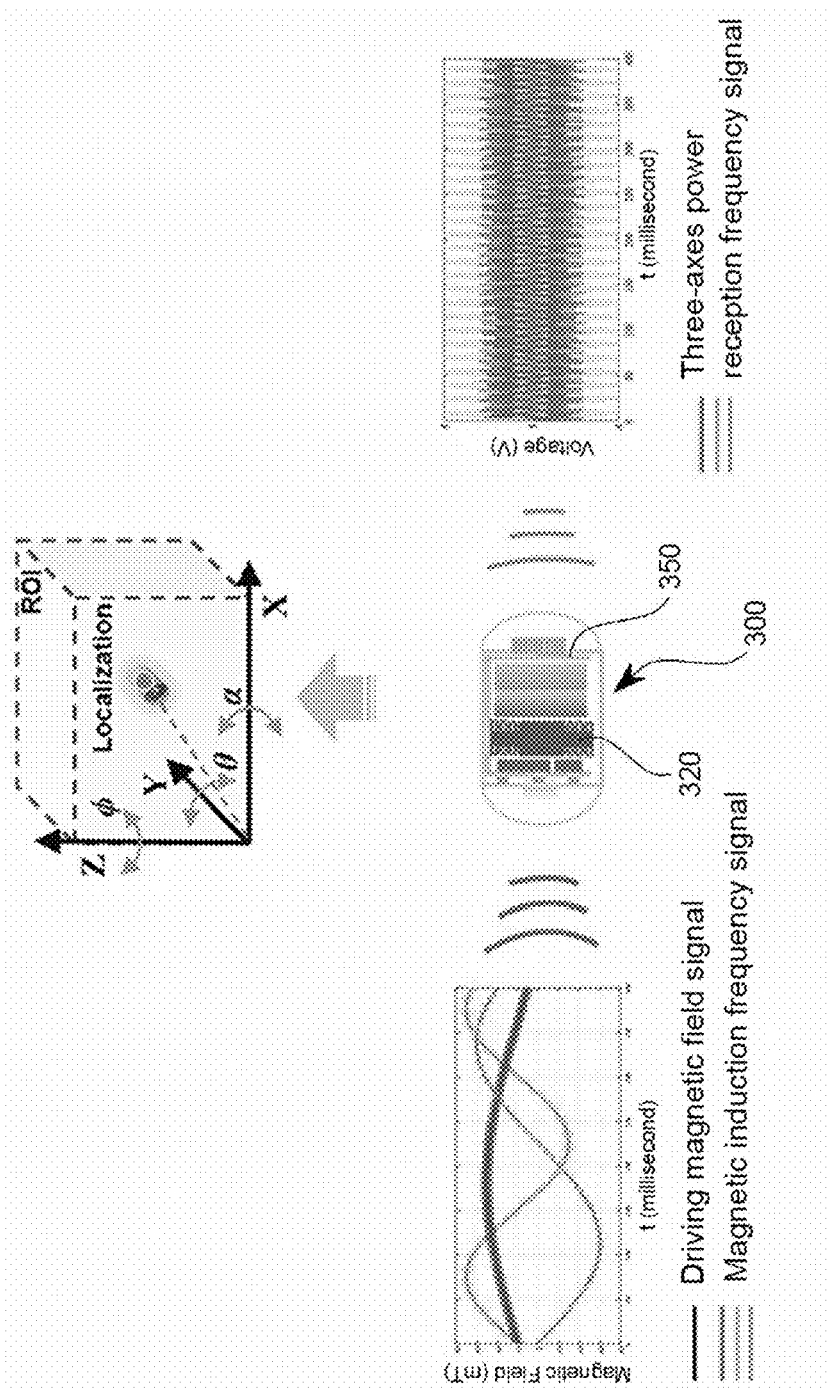
FIG. 12 is a diagram illustrating recognition of the location of a capsule endoscope in 6 degrees of freedom through a micro-robot control apparatus according to the present disclosure.

As shown in FIG. 12, when a magnetic induction frequency signal is applied to the magnetic induction reception coil 320 of the capsule endoscope 300 through the magnetic induction transmission coil 130, a magnetic induction reception frequency signal is transmitted to the micro-robot control apparatus 1 through the RF coil 350 depending on the power reception efficiency of the charging module 340 according to the difference in the distance.

The micro-robot control apparatus 1 recognizes the location of the capsule endoscope 300 from the received magnetic induction reception frequency signal. That is, the amount of electromotive force induced from the endoscope 300 is converted based on distance, thereby recognizing the location of the capsule endoscope 300 in 6 degrees of freedom.

At this time, the location of the capsule endoscope 300 in 6 degrees of freedom recognized by the micro-robot control apparatus 1 includes three-dimensional coordinate information (information on three locations on the x-axis, y-axis, and z-axis) and rotational angle information at the respective coordinates (information on three angles of $\alpha$, $\theta$, and $\varphi$).

The three-axes electromotive force (V) of the capsule endoscope 300 induced by the magnetic induction transmission coil 130 may be converted into a magnetic flux (Wb), and the magnetic flux (Wb) may be converted into a magnetic field (B) generated in the magnetic induction transmission coil 130.

The magnetic induction transmission coil 130 may form a magnetic field (B) depending on the distance values on the x-, y-, and z-axes from the inner center point, may match the 3-axis magnetic flux (Wb) converted from the induced electromotive force (V) and the 3-axis magnetic field (B) of the magnetic induction transmission coil 130, and may then recognize the three-dimensional coordinate information (information on three locations on the x-axis, y-axis, and z-axis) and the rotational angle information at the respective coordinates (information on three angles of $\alpha$, $\theta$, and $\varphi$) of the capsule endoscope 300 from the inner center of the magnetic induction transmission coil 130.

Therefore, since the location recognition system of the capsule endoscope has a feature capable of simultaneously realizing generation of wireless power of the capsule endoscope 300 and location recognition thereof, and enables recognition of the location of the capsule endoscope 300 in 6 degrees of freedom (three locations and three angles), it is possible to implement technical features capable of solving locational errors caused by the characteristics of the human body and the characteristics of a sensor device.

Figure 13:
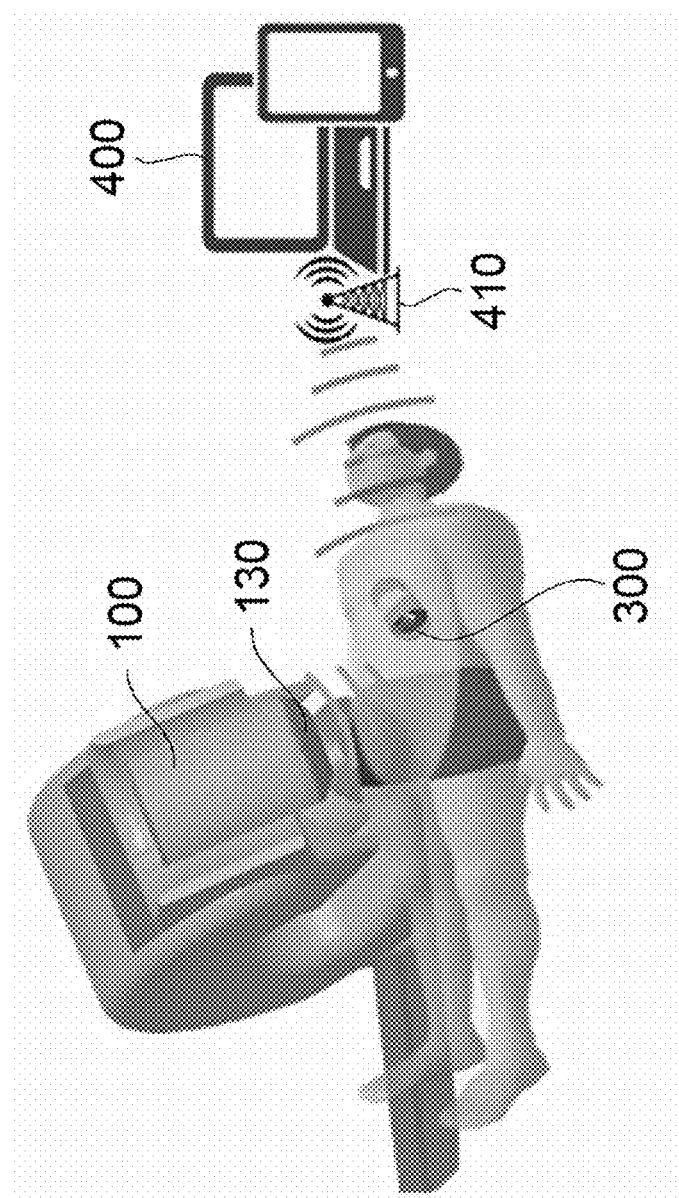
FIG. 13 is a block diagram schematically illustrating the configuration of a location recognition system of a capsule endoscope according to another embodiment of a micro-robot control apparatus according to the present disclosure.

FIG. 13 schematically illustrates the configuration of a location recognition system of a capsule endoscope according to another embodiment of a micro-robot control apparatus 1 equipped with two electromagnetic modules and a magnetic induction transmission coil for generating a magnetic induction frequency signal for recognizing the location of a micro-robot according to the present disclosure. Referring to the drawing, the micro-robot control apparatus 1 may include an electromagnetic module 100 for driving the capsule endoscope 300 and a magnetic induction transmission coil 130 that generates a magnetic induction frequency signal to recognize the location of a capsule endoscope 300. The magnetic induction transmission coil 130 may be installed in a bed (not shown) as a single device, or may be configured as being coupled to the electromagnetic module 100.

A magnetic induction reception frequency signal induced by the capsule endoscope 300 using the magnetic induction transmission coil 130 is transmitted to a main computer 400 through an RF receiver 410.

The main computer 400 may formulate the amount of electromotive force based on distance, and may identify the distance and direction of the capsule endoscope 200 from the magnetic induction transmission coil 320, thereby recognizing the exact location of the capsule endoscope 300.

Figure 14:
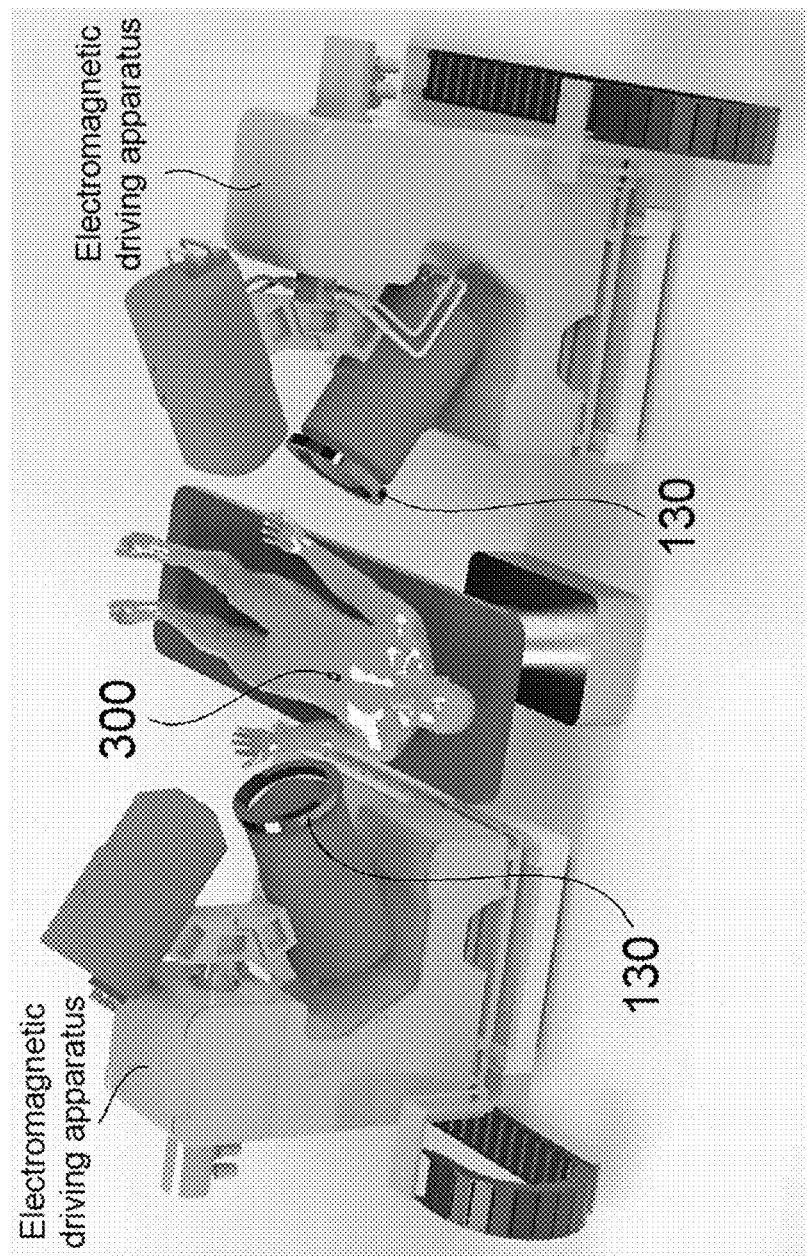
FIG. 14 illustrates an example in which a micro-robot location recognition system is applied to a micro-robot driving system other than the micro-robot control apparatus of the present disclosure.

Meanwhile, the micro-robot location recognition system of the present disclosure may be applied to any device for controlling a micro-robot using an electromagnetic field, as well as the micro-robot control apparatus 1 of the present disclosure. As shown in FIG. 14, even in the case where two or more electromagnetic driving devices are disposed to generate an electromagnetic field, it is possible to accurately recognize the location of the capsule endoscope by installing the magnetic induction transmission coil to some coils and installing the magnetic induction reception coil to the capsule endoscope. A specific method of recognizing the location has already been described above.

Although the present disclosure has been described with reference to the embodiments shown in the drawings, these are only provided by way of example, and those of ordinary skill in the art will understand that various modifications and equivalent embodiments may be derived therefrom. Therefore, the true technical protection scope of the present disclosure must be determined by the technical spirit of the appended claims.

INDICATION OF REFERENCE NUMERALS

1: Micro-robot control apparatus
100: Electromagnetic module
110: Solenoid coil
120: Magnetic core
121: Core protrusion
130: Location recognition transmission coil
200: Spherical paramagnet
300: Capsule endoscope
310: Body
320: Magnetic induction reception coil
330: Magnet
340: Charging module
350: RF coil
400: Main computer
410: RF receiver.

INDUSTRIAL APPLICABILITY

The present disclosure relates to a micro-robot control apparatus.

What is claimed is:

1. An electromagnetic system for focusing a magnetic field, the electromagnetic system comprising
two electromagnetic modules each comprising a magnetic core made of a paramagnet and a solenoid coil wound around the magnetic core,
wherein the two electromagnetic modules are configured to be disposed to be symmetrical with each other with respect to an imaginary symmetric axis passing through a center of an area of interest, where the magnetic field is desired to be focused, on a two-dimensional plane including the imaginary symmetric axis,
wherein a core protrusion is formed at one end of each electromagnetic module, which is configured to be directed to the area of interest, and
wherein the core protrusion of each electromagnetic module has a cylindrical shape having the same diameter as the outer diameter of each solenoid coil.

2. The electromagnetic system for focusing a magnetic field of claim 1, further comprising a rotatable spherical paramagnet configured to be disposed in a space between the core protrusions of the two electromagnetic modules and the area of interest.

3. The electromagnetic system for focusing a magnetic field of claim 1, wherein the core protrusions of the two electromagnetic modules are disposed adjacent to each other.

4. The electromagnetic system for focusing a magnetic field of claim 1, wherein the diameter of a portion of each electromagnetic module at which a protrusion starts in the core protrusion is the same as the inner diameter of each solenoid coil.

5. A micro-robot control apparatus comprising:
the electromagnetic system according to claim 1;
a power source configured to supply power to the solenoid coils of the electromagnetic system; and
a moving part configured to control a rotational motion and a three-dimensional linear motion of the electromagnetic system with respect to the imaginary symmetric axis.

6. A micro-robot control apparatus comprising:
two electromagnetic modules each comprising a magnetic core made of a paramagnet that are configured to be disposed to be symmetrical with each other with respect to an imaginary symmetric axis passing through a center of an area of interest, where a magnetic field is desired to be focused, on a two-dimensional plane including the imaginary symmetric axis, and a solenoid coil wound around the magnetic core;
a magnetic induction transmission coil configured to generate a magnetic induction frequency signal for recognizing a location of a micro-robot; and
a power source configured to supply power to the solenoid coils and the magnetic induction transmission coil,
wherein a core protrusion is formed at one end of each electromagnetic module, which is configured to be directed to the area of interest, and
wherein the core protrusion of each electromagnetic module has a cylindrical shape having the same diameter as the outer diameter of each solenoid coil.

7. The micro-robot control apparatus of claim 6, further comprising a moving part configured to control a rotational motion and a three-dimensional linear motion of the electromagnetic system with respect to the imaginary symmetric axis.

8. The micro-robot control apparatus of claim 6, further comprising the micro-robot equipped with a magnetic induction frequency signal reception coil for recognition of location.

9. The micro-robot control apparatus of claim 6, further comprising a rotatable spherical paramagnet configured to be disposed in a space between the core protrusions of the two electromagnetic modules and the area of interest.

10. The micro-robot control apparatus of claim 6, wherein the core protrusions of the two electromagnetic modules are disposed adjacent to each other.

11. The micro-robot control apparatus of claim 6, wherein the diameter of a portion at which a protrusion of each electromagnetic module starts in the core protrusion is the same as the inner diameter of each solenoid coil.

12. The micro-robot control apparatus according to claim 6, wherein the magnetic induction transmission coil applies a magnetic induction frequency signal to the micro-robot, and
wherein the micro-robot control apparatus receives an amount of electromotive force induced by the micro-robot and then recognizes the location of the micro-robot in 6 degrees of freedom.

13. The micro-robot control apparatus of claim 12, wherein the amount of electromotive force induced by the micro-robot is converted based on distance to recognize the location of the micro-robot in 6 degrees of freedom.

14. The micro-robot control apparatus of claim 13, wherein the location of the micro-robot in 6 degrees of freedom recognized by the micro-robot control apparatus comprises three-dimensional coordinate information and rotational angle information at respective coordinates.

15. The micro-robot control apparatus of claim 12, wherein the micro-robot is a capsule endoscope comprising:
a body in a form of a capsule;
a magnetic induction frequency signal reception coil configured to generate induction power from the magnetic induction frequency signal applied for recognition of location;
a charging module configured to be charged by the induction power;
a magnet configured to interact with the magnetic field; and
an RF (radio frequency) coil configured to transmit a frequency signal of the induction power generated from the magnetic induction frequency signal reception coil to the micro-robot control apparatus.

16. A micro-robot control apparatus comprising:
two electromagnetic modules each comprising a magnetic core made of a paramagnet that are configured to be disposed to be symmetrical with each other with respect to an imaginary symmetric axis passing through a center of an area of interest, where a magnetic field is desired to be focused, on a two-dimensional plane including the imaginary symmetric axis, and a solenoid coil wound around the magnetic core;
a magnetic induction transmission coil configured to generate a magnetic induction frequency signal for recognizing a location of a micro-robot;
a power source configured to supply power to the solenoid coils and the magnetic induction transmission coil;
a moving part configured to control a rotational motion and a three-dimensional linear motion of the electromagnetic system with respect to the imaginary symmetric axis; and
the micro-robot equipped with a magnetic induction frequency signal reception coil for recognition of location,
wherein a core protrusion is formed at one end of each electromagnetic module, which is configured to be directed to the area of interest, and
wherein the core protrusion of each electromagnetic module has a cylindrical shape having the same diameter as the outer diameter of each solenoid coil.

17. The micro-robot control apparatus of claim 16, further comprising a rotatable spherical paramagnet configured to be disposed in a space between the core protrusions of the two electromagnetic modules and the area of interest.

18. The micro-robot control apparatus of claim 16, wherein the core protrusions of the two electromagnetic modules are disposed adjacent to each other.

19. The micro-robot control apparatus of claim 16, wherein the diameter of a portion at which a protrusion of each electromagnetic module starts in the core protrusion is the same as the inner diameter of each solenoid coil.

20. The micro-robot control apparatus of claim 16, wherein the magnetic induction transmission coil applies a magnetic induction frequency signal to the micro-robot, and
wherein the micro-robot control apparatus receives an amount of electromotive force induced by the micro-robot and then recognizes the location of the micro-robot in 6 degrees of freedom.

21. The micro-robot control apparatus of claim 16, wherein the amount of electromotive force induced by the micro-robot is converted based on distance to recognize the location of the micro-robot in 6 degrees of freedom.

22. The micro-robot control apparatus of claim 16, wherein the location of the micro-robot in 6 degrees of freedom recognized by the micro-robot control apparatus comprises three-dimensional coordinate information and rotational angle information at respective coordinates.

23. The micro-robot control apparatus of claim 16, wherein the micro-robot is a capsule endoscope comprising:
a body in a form of a capsule;
a magnetic induction frequency signal reception coil configured to generate induction power from the magnetic induction frequency signal applied for recognition of the location;
a charging module configured to be charged by the induction power;
a magnet configured to interact with the magnetic field; and
an RF (radio frequency) coil configured to transmit a frequency signal of the induced power generated from the magnetic induction frequency signal reception coil to the micro-robot control apparatus.

* * * * *